US008669418B2

(12) United States Patent
Schymkowitz et al.

(10) Patent No.: US 8,669,418 B2
(45) Date of Patent: *Mar. 11, 2014

(54) MEANS AND METHODS FOR MEDIATING PROTEIN INTERFERENCE

(75) Inventors: Joost Schymkowitz, Meensel-Kiezegem (BE); Frederic Rousseau, Groot-Bijgaarden (BE)

(73) Assignees: VIB VZW, Gent (BE); Vrije Universiteit Brussel, Brussel (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/102,381

(22) Filed: May 6, 2011

(65) Prior Publication Data

US 2012/0023624 A1 Jan. 26, 2012

Related U.S. Application Data

(63) Continuation-in-part of application No. 12/214,761, filed on Jun. 20, 2008, which is a continuation of application No. PCT/EP2006/070184, filed on Dec. 22, 2006.

(60) Provisional application No. 60/753,245, filed on Dec. 22, 2005, provisional application No. 60/872,079, filed on Dec. 1, 2006.

(30) Foreign Application Priority Data

Dec. 22, 2005 (EP) .................... 05112761
Dec. 1, 2006 (EP) .................... 06125189

(51) Int. Cl.
*A01H 5/00* (2006.01)
*C07K 4/00* (2006.01)
*C07K 2/00* (2006.01)
*C12N 15/115* (2010.01)
*C12N 15/63* (2006.01)
*C12Q 1/68* (2006.01)

(52) U.S. Cl.
USPC ......... 800/278; 536/24.2; 536/24.5; 530/300; 530/305; 530/333; 530/387.9; 435/455; 435/468; 435/463; 706/13; 977/705; 977/839

(58) Field of Classification Search
None
See application file for complete search history.

(56) References Cited

U.S. PATENT DOCUMENTS

| | | | |
|---|---|---|---|
| 4,186,183 A | 1/1980 | Steck et al. | |
| 4,217,344 A | 8/1980 | Vanlerberghe et al. | |
| 4,235,871 A | 11/1980 | Papahadjopoulos et al. | |
| 4,261,975 A | 4/1981 | Fullerton et al. | |
| 4,485,054 A | 11/1984 | Mezei et al. | |
| 4,501,728 A | 2/1985 | Geho et al. | |
| 4,550,017 A | 10/1985 | Liu et al. | |
| 4,774,085 A | 9/1988 | Fidler | |
| 4,797,368 A | 1/1989 | Carter et al. | |
| 4,837,028 A | 6/1989 | Allen | |
| 4,897,355 A | 1/1990 | Eppstein et al. | |
| 4,946,787 A | 8/1990 | Eppstein et al. | |
| 5,049,386 A | 9/1991 | Eppstein et al. | |
| 5,173,414 A | 12/1992 | Lebkowski et al. | |
| 6,159,748 A | 12/2000 | Hechinger | |
| 6,372,967 B1 * | 4/2002 | Mariani et al. | 800/303 |
| 6,399,317 B1 | 6/2002 | Weimer | |
| 6,489,092 B1 | 12/2002 | Benjamin et al. | |
| 6,627,616 B2 | 9/2003 | Monahan et al. | |
| 6,682,940 B2 | 1/2004 | Pankowsky | |
| 2002/0098173 A1 | 7/2002 | Findeis et al. | |
| 2005/0026165 A1 | 2/2005 | Orser et al. | |
| 2005/0203010 A1 * | 9/2005 | Kim | 514/12 |

FOREIGN PATENT DOCUMENTS

| | | |
|---|---|---|
| WO | WO 91/16024 | 10/1991 |
| WO | WO 91/17424 | 11/1991 |
| WO | WO 93/24641 | 12/1993 |
| WO | WO 03/102187 A1 | 12/2003 |
| WO | WO 2007/071789 A1 | 6/2007 |

OTHER PUBLICATIONS

Prasanna et al (Biochemistry, 1998, 37, p. 6883-6893).*
Nagel-Wolfrum et al (Molecular Cancer Research, vol. 2, Mar. 2004, p. 170-182).*
Esteras-Chopo et al (PNAS, Nov. 15, 2005, 102(46) p. 16672-16677).*
Chi et al (Pharmaceutical Res. 20:2003, p. 1326-1336).*
Lam et al (The Plant Cell, vol. 13, 2499-2512, Nov. 2001).*
Lopez de la Paz et al (PNAS, 2002, 99(25) p. 16052-16057).*
Yoon et al., "Detecting hidden sequence propensity for amyloid fibril formation," *Protein Science*, vol. 13, pp. 2149-2160, 2004.
Esteras-Chopo et al., "The amyloid stretch hypothesis: Recruiting proteins toward the dark side," *PNAS*, vol. 102, No. 46, pp. 16672-16677, Nov. 15, 2005.
Sánchez De Groot et al., "Prediction of "hot spots" of aggregation in disease-linked polypeptides," *BMC Structural Biology*, vol. 5, No. 18, pp. 1-15, Sep. 30, 2005.
Tartaglia et al., "Prediction of aggregation rate and aggregation-prone segments in polypeptide sequences," *Protein Science*, vol. 14, pp. 2723-2734, 2005.
Ventura et al., "Short amino acid stretches can mediate amyloid formation in globular proteins: The Src homology 3 (SH3) case," *PNAS*, vol. 101, No. 19, pp. 7258-7263, May 11, 2004.
Yudt et al., "Preventing estrogen receptor action with dimer-interface peptides," Steroids vol. 66, pp. 549-558, 2001.
Chi et al., "Physical Stability of Proteins in Aqueous Solution: Mechanism and Driving Forces in Nonnative Protein Aggregation," Pharmaceutical Research, vol. 20, No. 9, pp. 1325-1336, 2003.
Fernandez-Escamilla et al., "Prediction of sequence-dependent and mutational effects on the aggregation of peptides and proteins," *Nature Biotechnology*, vol. 22, No. 10, pp. 1302-1306, Oct. 2004.

(Continued)

*Primary Examiner* — Anne Marie Grunberg
*Assistant Examiner* — Lee A Visone
(74) *Attorney, Agent, or Firm* — Foley & Lardner LLP

(57) ABSTRACT

The present invention belongs to the field of functional proteomics and more particularly to the field of protein aggregation. The invention discloses a method for interfering with the function of a target protein and uses a non-naturally, user-designed molecule, designated as interferor, that has a specificity for a target protein and which induces aggregation upon contact with said target protein. The present invention also discloses such interferor molecules and their use in agrobiotech applications.

9 Claims, 17 Drawing Sheets

(56) References Cited

OTHER PUBLICATIONS

Figure 1A:
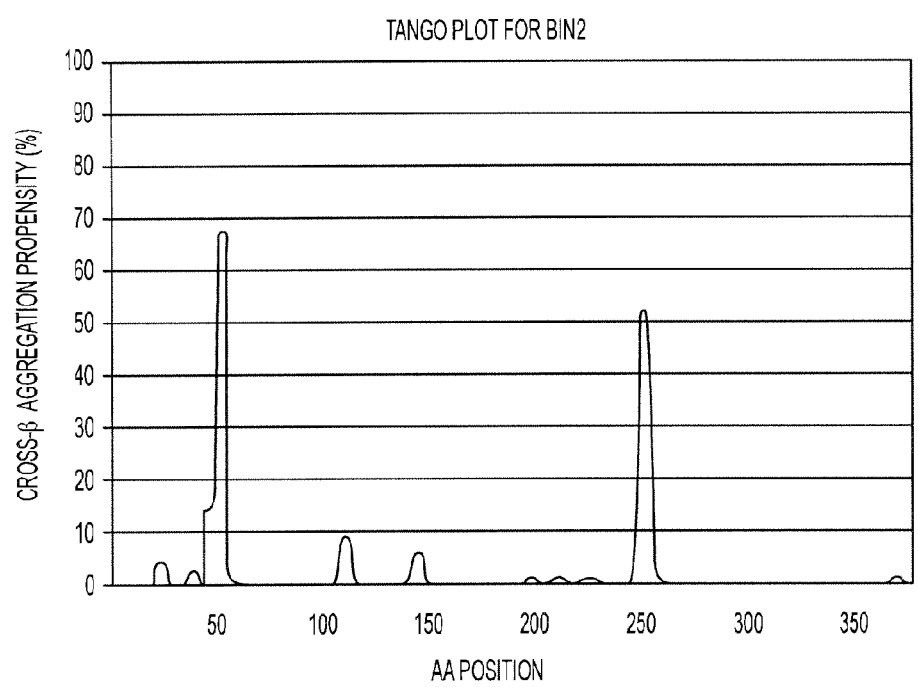

Bairoch et al., "The Universal Protein Resource (UniProt)," *Nucleic Acids Research*, vol. 33, Database issue, D154-D159, 2005.
Barral et al., "Roles of molecular chaperones in protein misfolding diseases," *Seminars in Cell & Developmental Biology*, vol. 15, pp. 17-29, 2004.
Chiti et al., "Rationalization of the effects of mutations on peptide and protein aggregation rates," *Nature*, vol. 424, pp. 805-808, Aug. 14, 2003.
Clark, "Protein aggregation determinants from a simplified model: Cooperative folders resist aggregation," *Protein Science*, vol. 14, pp. 653-662, 2005.
De Marco et al., "The solubility and stability of recombinant proteins are increased by their fusion to NusA," *Biochemical and Biophysical Research Communications*, vol. 322, pp. 766-771, 2004.
Dobson, "Getting out of shape," *Nature*, vol. 418, pp. 729-730, Aug. 15, 2002.
Dobson, "Principles of protein folding, misfolding and aggregation," *Seminars in Cell & Developmental Biology*, vol. 15, pp. 3-16, 2004.
Guex et al., "SWISS-MODEL and the Swiss-Pdb Viewer: An environment for comparative protein modeling," *Electrophoresis*, vol. 18, pp. 2714-2723, 1997.
Pawar et al., "Prediction of "Aggregation-prone" and "Aggregation-susceptible" Regions in Proteins Associated with Neurodegenerative Diseases," *J. Mol. Biol.*, vol. 350, pp. 379-392, 2005.
Hamada et al., "Engineering amyloidogenicity towards the development of nanofibrillar materials," *Trends in Biotechnology*, vol. 22, No. 2, pp. 93-97, Feb. 2004.
Houry et al., "Identification of in vivo substrates of the chaperonin GroEL," *Nature*, vol. 402, pp. 147-154, Nov. 11, 1999.

Kopp et al., "The SWISS-MODEL Repository of annotated three-dimensional protein structure homology models," *Nucleic Acids Research*, vol. 32, Database issue, pp. D230-D234, 2004.
Linding et al., "A Comparative Study of the Relationship Between Protein Structure and β-Aggregation in Globular and Intrinsically Disordered Proteins," *J. Mol. Biol.*, vol. 342, pp. 345-353, 2004.
López De La Paz et al., "Sequence determinants of amyloid fibril formation," *PNAS*, vol. 101, No. 1, pp. 87-92, Jan. 6, 2004.
Makin et al., "Molecular basis for amyloid fibril formation and stability," *PNAS*, vol. 102, No. 2, pp. 315-320, Jan. 11, 2005.
Nelson et al., "Structure of the cross-β spine of amyloid-like fibrils," *Nature*, vol. 435, pp. 773-778, Jun. 2005.
Barelle et al., "GFP as a quantitative reporter of gene regulation in *Candida albicans*," *Yeast*, vol. 21, pp. 333-340, 2004.
Leuker et al., "Sequence and promoter regulation of the *PCK1* gene encoding phosphoenolpyruvate carboxykinase of the fungal pathogen *Candida albicans*," *Gene*, vol. 192, pp. 235-240, 1997.
Fonzi et al., "Isogenic Strain Construction and Gene Mapping in *Candida albicans*," *Genetics*, vol. 134, pp. 717-728, Jul. 1993.
Kizana et al., "Therapeutic Prospects of Cardiac Gene Transfer," Heart, Lung and Circulation, vol. 16, pp. 180-184, 2007.
Lee et al., "Production of recombinant amyloid-β peptide 42 as an ubiquitin extension," Protein Expression and Purification, vol. 40, pp. 183-189, 2005.
PCT International Search Report issued in PCTIEP2006/070184, dated Mar. 16, 2007.
Office Action issued by the Examiner in U.S. Appl. No. 12/214,761, filed Sep. 3, 2010.
Office Action issued by the Examiner in U.S. Appl. No. 12/214,761, filed Apr. 6, 2010.
Office Action issued by the Examiner in U.S. Appl. No. 12/214,761, filed Nov. 30, 2009.

* cited by examiner

A

SEQUENCE LISTING

```
<160> NUMBER OF SEQ ID NOS: 31

<210> SEQ ID NO 1
<211> LENGTH: 13
<212> TYPE: PRT
<213> ORGANISM: Artificial Sequence
<220> FEATURE:
<223> OTHER INFORMATION: Bait region of BIN2

<400> SEQUENCE: 1
```

-continued

Arg Val Val Gly Thr Gly Ser Phe Gly Ile Val Phe Lys
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Bait region of BIN2

<400> SEQUENCE: 2

Gln Leu Val Glu Ile Ile Lys Val Leu
1               5

<210> SEQ ID NO 3
<211> LENGTH: 11
<212> TYPE: PRT
<213> ORGANISM: Artificial Sequence
<220> FEATURE:
<223> OTHER INFORMATION: Bait region of BIN2 with charged arginine
      residues

<400> SEQUENCE: 3

Arg Gln Leu Val Glu Ile Ile Lys Val Leu Arg
1               5                   10

<210> SEQ ID NO 4
<211> LENGTH: 28
<212> TYPE: PRT
<213> ORGANISM: Artificial Sequence
<220> FEATURE:
<223> OTHER INFORMATION: Synthetic sequence booster of aggregation

<400> SEQUENCE: 4

Gln Trp Gln Asn Ser Thr Leu Ile Val Leu Gln Asn Ser Thr Val Ile
1               5                   10                  15

Phe Glu Gln Asn Ser Thr Val Ile Phe Glu Gln Asn
            20                  25

<210> SEQ ID NO 5
<211> LENGTH: 12
<212> TYPE: PRT
<213> ORGANISM: Artificial Sequence
<220> FEATURE:
<223> OTHER INFORMATION: flexible linker sequence

<400> SEQUENCE: 5

Lys Pro Ala Gly Ala Ala Lys Pro Gly Ala Ala Gly
1               5                   10

<210> SEQ ID NO 6
<211> LENGTH: 21
<212> TYPE: PRT
<213> ORGANISM: Artificial Sequence
<220> FEATURE:
<223> OTHER INFORMATION: Bait region of BIN2

<400> SEQUENCE: 6

Glu Asn Ala Val Asp Gln Leu Val Glu Ile Ile Lys Val Leu Gly Thr
1               5                   10                  15

Pro Thr Arg Glu Glu
            20

<210> SEQ ID NO 7
<211> LENGTH: 6
<212> TYPE: PRT
<213> ORGANISM: Artificial Sequence

```
<220> FEATURE:
<223> OTHER INFORMATION: Begin of BIN2

<400> SEQUENCE: 7

Met Ala Asp Asp Lys Glu
1               5

<210> SEQ ID NO 8
<211> LENGTH: 15
<212> TYPE: PRT
<213> ORGANISM: Artificial Sequence
<220> FEATURE:
<223> OTHER INFORMATION: flexible linker sequence

<400> SEQUENCE: 8

Ala Gly Ser Pro Lys Gly Ala Pro Ala Ala Lys Gly Ser Gly Ala
1               5                   10                  15

<210> SEQ ID NO 9
<211> LENGTH: 42
<212> TYPE: PRT
<213> ORGANISM: Artificial Sequence
<220> FEATURE:
<223> OTHER INFORMATION: Tandem repeat bait

<400> SEQUENCE: 9

Glu Asn Ala Val Asp Gln Leu Val Glu Ile Ile Lys Val Leu Gly Thr
1               5                   10                  15

Pro Thr Arg Glu Glu Glu Asn Ala Val Asp Gln Leu Val Glu Ile Ile
            20                  25                  30

Lys Val Leu Gly Thr Pro Thr Arg Glu Glu
        35                  40

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
gtgatctcag ccgtacattt gga                                       23

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
cacgtcgaaa aactaccact tcct                                      24

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gaatggagtg attacaagtc                                           20

<210> SEQ ID NO 13
<211> LENGTH: 22
<212> TYPE: DNA
```

```
<213> ORGANISM: Artificial Sequence
<220> FEATURE:
<223> OTHER INFORMATION: Primer

<400> SEQUENCE: 13
gtgaacacat tagaagggcc tg                                              22

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ctcatttgcc aatcctgtat c                                               21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gcactgagat gcgacatctt g                                               21

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
tgactcttat ccgcttgaac ag                                              22

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
tcctacgttg ctttcactga c                                               21

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
gtggttcctt cactgtcact ag                                              22

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
ttcaccaagt ctttgagtct cc                                              22
```

```
<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tgaaaggaag aggatgcagc                                              20

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
tgtatttcat cgtgagaggc tg                                           22

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gctattctca gcggtgaagg                                              20

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
ttctcgtctt ggatggtgtt c                                            21

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gaaacagaac cactccctcg                                              20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
ccaatcaacc tctttgcatc g                                            21

<210> SEQ ID NO 26
<211> LENGTH: 21
<212> TYPE: DNA
<213> ORGANISM: Artificial Sequence
<220> FEATURE:
<223> OTHER INFORMATION: Primer
```

```
<400> SEQUENCE: 26
aacagaacca caccgtctta c                                              21

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
accaatcaac ctcttcgcat c                                              21

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
attgcgtatt gccactctca tagg                                           24

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
tcctgacagg gataccgaat gc                                             22

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
ctggaggttt tgaggctggt at                                             22

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
ccaaggctga aagcaagaag a                                              21
```

MEANS AND METHODS FOR MEDIATING PROTEIN INTERFERENCE

FIELD OF THE INVENTION

The present invention belongs to the field of functional proteomics and more particularly to the field of protein aggregation. The invention discloses a method for interfering with the function of a target protein and uses a non-naturally, user-designed molecule, designated as interferor, that has a specificity for a target protein and which induces aggregation upon contact with said target protein. The present invention also discloses such interferor molecules and their use in agro-biotech applications.

BACKGROUND OF THE INVENTION

Biology is entering an exciting era brought about by the increase in genome-wide information. As genome sequencing and high-throughput functional genomics approaches generate more and more data, researchers need new ways to tease out biological relevant information. Functional genomics in particular is making rapid progress in assigning biological meaning to genomic data. The information encoded in the genome comprises genes, the protein products of which mediate most of the functions in organisms, and control elements. Proteins were thought to be the most important effectors in the cells, although recently non-coding RNAs have also been identified as important players in regulatory processes.

Several key biological questions are central to continuing genome projects and are relevant to any cellular organism, from bacteria to humans. One challenge is to understand how genes that are encoded in a genome operate and interact to produce a complex living system. A related challenge is to determine the function of all the sequence elements in the genome. The toolbox of functional genomics has enabled several systematic approaches that can provide the answers to a few basic questions for the majority of genes in a genome, including when is a gene expressed, where its product is localized, with which other gene products does it interact and what phenotype results if a gene is mutated. Phenotypic analysis of mutants has been a powerful approach for determining gene function. Gene function can be altered through gene deletions, insertional mutagenesis and RNA interference (RNAi). RNAi is a relatively recent development for reducing gene expression. It follows reports of gene silencing in plants and other model organisms, and is based on the observation from *C. elegans* that adding double-stranded RNA (dsRNA) to cells often interferes with gene function in a sequence-specific manner. In many cases, the level of functional reduction cannot be adequately controlled, is incomplete, the level of specificity is not entirely predictable and in some organisms RNAi does not work (e.g. in the yeast *Candida albicans*).

It is obvious that functional genomics has changed the way biology is done and yet the field is still in its infancy in terms of detailing the complexity that underlies biological systems, such as the complex network of genetic regulation, protein interactions and biochemical reactions that make up a cell. Clearly there is a need to develop innovative technologies, especially in the field of functional proteomics, in order to accelerate discoveries and to maximize the potential offered by complementary methods in functional genomics. It would be desirable to possess a flexible technology that can directly target the biological function of a particular extracellular or intracellular protein instead of targeting the mRNA that translates it or manipulating the gene that encodes it.

The conversion of normally soluble proteins into conformationally altered insoluble proteins is thought to be a causative process in a variety of diseases such as for example the occurrence of amyloid beta peptide in Alzheimer's disease and cerebral amyloid angiopathy, alpha-synuclein deposits in Lewy bodies of Parkinson's disease, prions in Creutzfeldt-Jacob disease, superoxide dismutase in amyotrophic lateral sclerosis and tau in neurofibrillary tangles in frontal temporal dementia and Pick's disease. Thus far, protein aggregation has mainly been studied as an unwanted, disease-causing phenomenon and it is widely accepted that cross-beta mediated aggregation is the most frequently occurring and biologically relevant mechanism of aggregation[2]. Cross-beta aggregation is the term used to indicate that aggregation is nucleated via the formation of intermolecular beta-sheets to which each molecule in the aggregate contributes an identical strand of typically comprising at least three contiguous amino acids. There is now abundant data to show that the individual strands interact to form an intermolecular beta sheet and that this structure forms the backbone of the aggregate[3,4]. Self-association regions in target proteins can be determined by computer programs, such as TANGO[6], which were developed for predicting the aggregation propensity of peptides and proteins. One specific form of aggregation, namely the highly ordered amyloid fibre, is already being explored in the art for potential use in the material sciences[5]. In addition, WO03102187 (Scegen, Pty Ltd) discloses a method for enhancing the activity of a molecule by fusing said molecule with a membrane translocating sequence, whereby the resulting chimeric molecule self-assembles into a higher molecular weight aggregate. US20050026165 (Areté Associates) discloses the use of conformational peptides, able to interact with the beta-sheet conformation of insoluble proteins such as prions, as a diagnostic tool for prion diseases.

SUMMARY OF THE INVENTION

The present invention relates to a technology for the controlled and inducible protein aggregation of specific target proteins. The invention also provides de novo designed molecules, herein designated as interferor molecules, which comprise at least one aggregation region of which said aggregation region is derived from a target protein. In a preferred embodiment the interferor molecule comprises at least one self-association region that is fused to a moiety that prevents aggregation of said self-association region. Upon contact between a chosen target protein and a specifically designed interferor molecule, a specific co-aggregation occurs between the target and the interferor resulting in a functional knock-out or a down-regulation of the biological function for said target protein. This protein knock-down is conditional upon the presence of aggregates, which are induced by the presence of the interferor molecule. An additional advantage is that the strength of the protein interference can be experimentally controlled by varying the number of aggregation regions in the interferor molecule. The invention does not only provide an efficient tool to down-regulate the biological function of a specific extra- or intracellular protein but has also important therapeutic, agricultural and diagnostic applications.

In a first aspect the invention provides for a method for down-regulating the biological function of a protein in a plant or plant cell, the method comprising contacting said protein with a non-naturally occurring molecule, wherein said molecule comprises at least one beta-aggregation region derived from said target protein.

In a specific aspect the beta-aggregating region in the non-naturally occurring molecule is fused to a moiety that prevents aggregation of said β-aggregating region.

In a further specific aspect said moiety is a peptide or a protein domain.

In a further specific aspect the beta-aggregating region consists of at least 3 contiguous amino acids.

In yet a further specific aspect a polypeptide linker is present between the beta-aggregating region and a moiety that prevents aggregation of said β-aggregating region.

In yet a further specific aspect the non-naturally occurring molecule is a polypeptide encoded by a nucleotide sequence present on a recombinant vector and which, upon introduction into a plant cell or plant, produces said polypeptide in said plant cell or plant.

In yet a further specific aspect the invention provides for an artificial gene encoding a non-naturally occurring polypeptide wherein said polypeptide is comprises at least one beta-aggregation region isolated from a target protein.

In yet a further specific aspect the at least one beta-aggregation region encoded by the artificial gene consists of at least 3 contiguous amino acids.

In yet a further specific aspect the at least one beta-aggregation region encoded by the artificial gene is fused to a moiety that prevents aggregation of said beta-aggregation region.

In yet a further specific aspect the invention provides for a recombinant vector comprising an artificial gene encoding a non-naturally occurring polypeptide wherein said polypeptide comprises at least one beta-aggregation region isolated from a target protein.

In yet another specific aspect the invention provides for a plant or plant cell or plant seed comprising an artificial gene as described before or comprising a recombinant vector as described herein before.

FIGURE LEGENDS

FIG. 1. (a) TANGO plot diagram for BIN2; the peaks represent the peptide sequences with the highest propensity to aggregate within the BIN2 protein. (b) Schematic representation of the bait249 expression vectors containing a booster of aggregation N-terminally fused to GFP. The bait249 sequence is set forth in SEQ ID NO: 2, linker sequence is set forth in SEQ ID NO: 5, and booster sequence is set forth in SEQ ID NO: 4. The bait249R sequence is set forth in SEQ ID NO: 3, linker sequence is set forth in SEQ ID NO: 5, and booster sequence is set forth in SEQ ID NO: 4. (c) Representation of bait249 expression vectors including different linker and flanking sequences (aa sequences are indicated) but not containing any booster of aggregation. The bait249NF sequence is set forth in SEQ ID NO: 2, linker sequence is set forth in SEQ ID NO: 8, and natural flanks are set forth in SEQ ID NO: 9. The bait249NF_Tand sequence is set forth in SEQ ID NO: 2, linker sequence is set forth in SEQ ID NO: 8, and natural flanks are set forth in SEQ ID NO: 9.

Figure 2:
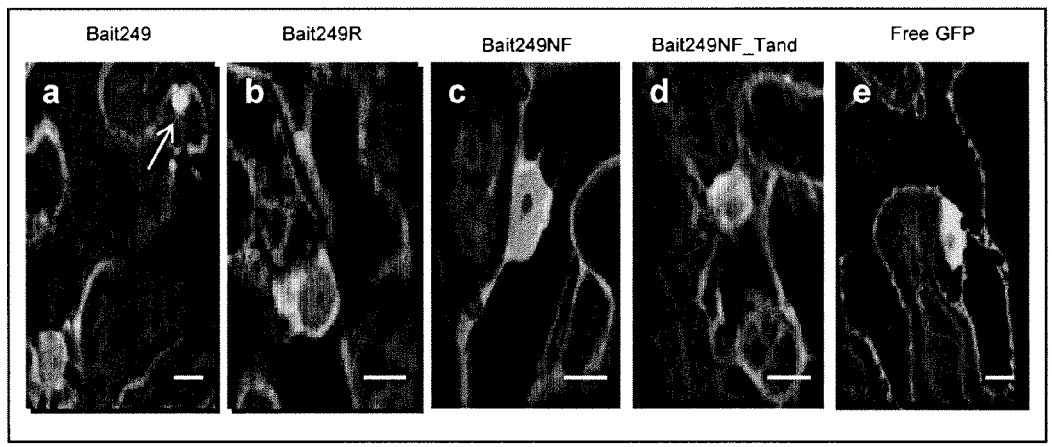

FIG. 2. (a-e) CLSM evaluation of aggregates formation in N. benthamiana agro-infiltrated leaves transiently transformed with the GFP expressing constructs indicated above each panel. Epidermal cells are GFP positive but show different localization patterns mainly in the perinuclear area. White arrow indicates an insoluble inclusion body. Size bars: 10 μm.

Figure 3:
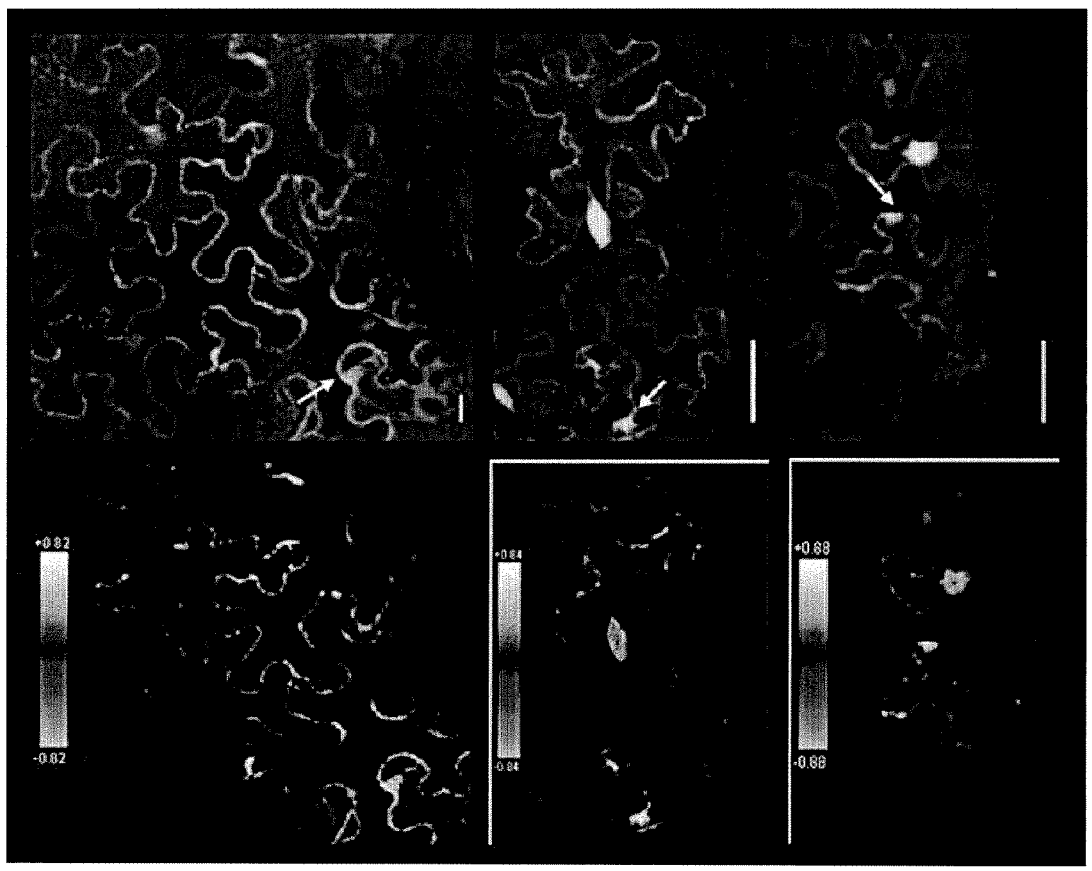

FIG. 3. Upper panel: CLSM images of N. benthamiana epidermal cells after 4.5 days from co-injection with 35SBIN2GFP and pMDCbait249NF_Tand expressing strains. In the bottom panel: corresponding images representing co-localization quantification performed by ImageJ MBF software. Mander's overlap coefficients (0<R<1) for each picture are indicated; size bars represent 50 μm.

Figure 4:
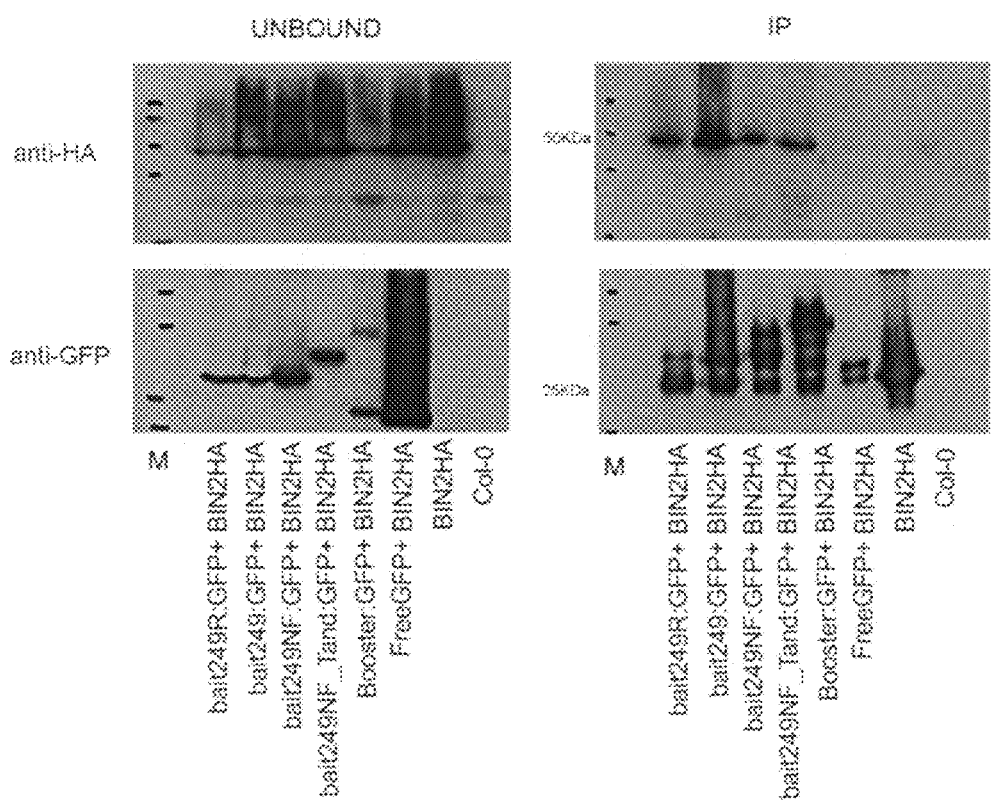

FIG. 4. Co-immunoprecipitation of 35S::bait249-GFP-variants co-expressed in N. benthamiana with 35S::BIN2:HA. In the left panel the Western blot detection of the unbound fractions of the plant proteins extracts after 4 hours of incubation with anti-GFP beads and detection with anti-HA antibody (left upper panel) or with anti-GFP antibodies (left low panel). In the right panel the detection of the Immuno Precipitated (IP) beads with anti-HA (right upper panel) or with anti-GFP antibody (right lower panel).

Figure 5:
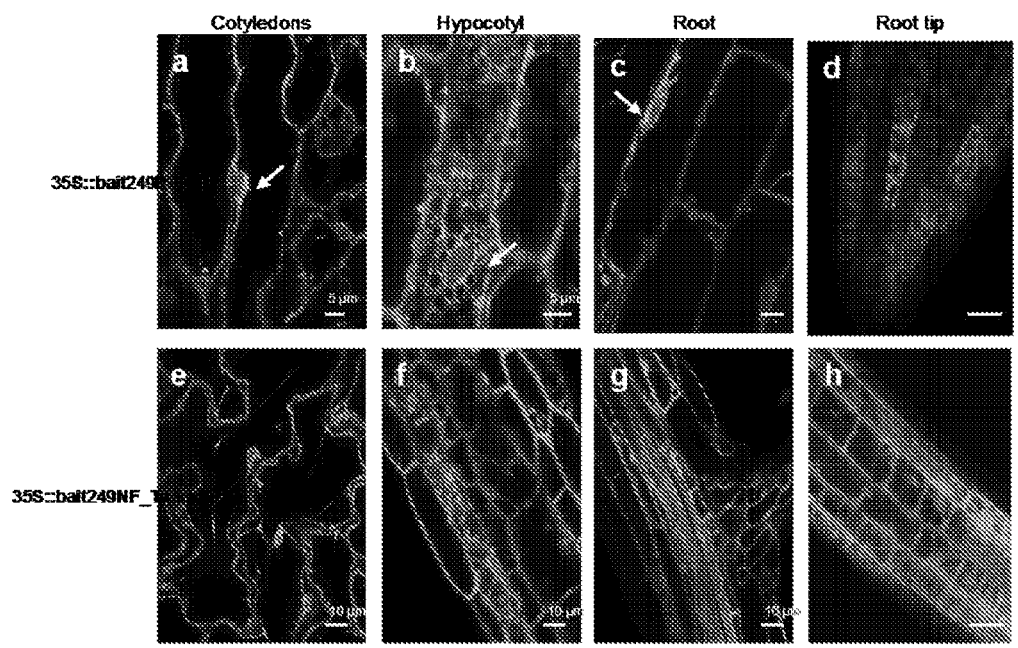

FIG. 5. (a-d) CLSM images of Arabidopsis 8 D.A.S. T3 seedlings expressing 35S::bait249R-GFP construct. Epidermal cells in cotyledons (a), hypocotyl (b) and root cells (c) show perinuclear aggregation (white arrows). The root tip shows no clear cytosolic aggregation and weak GFP signal (d). (e-h) CLSM images of Arabidopsis 8 D.A.S. T3 seedlings expressing 35S::bait249NF_Tand-GFP construct. Epidermal cells in cotyledons (e), hypocotyl (f) and root cells (g) show cytosolic aggregation. The root tip shows weaker GFP intensity (h). Size bars are indicated.

Figure 6:
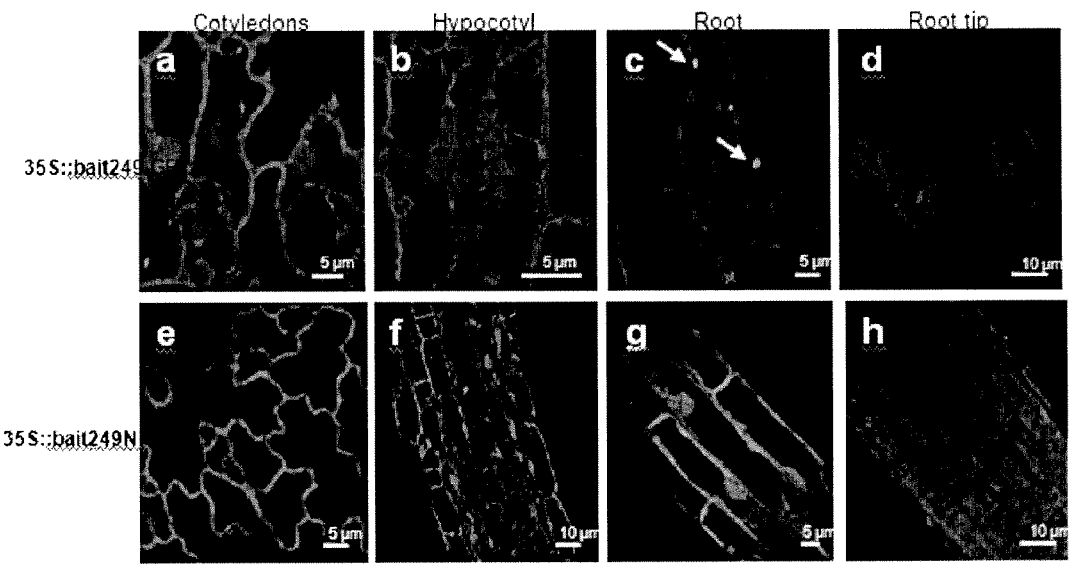

FIG. 6. (a-d) CLSM images of Arabidopsis 8 D.A.S. T3 seedlings expressing 35S::bait249-GFP construct. No clear aggregation is visible in plant tissues but only weak GFP expression is visible in cells in cotyledons (a), hypocotyls (b), and root tip (d). In root cells (c) the presence of insoluble aggregates in the form of round-shaped bodies is evidenced (white arrow). (e-h) CLSM images of Arabidopsis 8 D.A.S. T3 seedlings expressing 35S::bait249NF-GFP construct. The bait is expressed in any plant tissue showing perinuclear aggregation only in root cells (g). Size bars are indicated.

Figure 7:
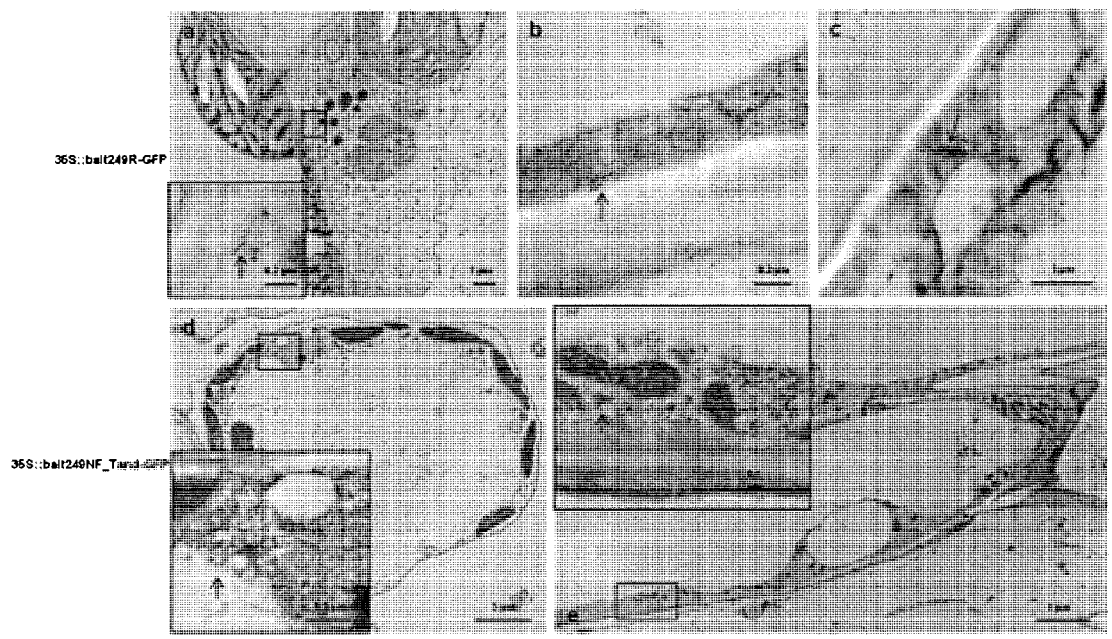

FIG. 7. TEM evaluation of immunogold labelled ultrathin section of 8 D.A.S. Arabidopsis seedlings incubated with an anti-GFP antibody. (a) Hypocotyl vascular parenchyma cell expressing 35S::bait249R-GFP showing labeled cytosolic fibrillar material (a) enlarged in the inset. (b-c) Details of root elongation area cells showing clustered labeling of bait249NF_Tand-GFP in the cytosol (b) and close to a Golgi stack (c). (d) Cotyledon palisade cell expressing bait249NF_Tand-GFP evidencing perinuclear labeling, enlarged in the inset. (e) Root elongation area cell showing cytoplasmic labeling of bait249NF_Tand in the cytosol. Size bars are indicated.

FIG. 8. (a) Native-PAGE and anti-GFP detection of high molecular weight complexes (framed) in protein extracts from transgenic Arabidopsis plants stably expressing the BIN2 bait249 lines respect to wild type (Col-0) plant extracts. (b,c) FT-IR spectroscopy on immuno-precipitated material from transgenic plants expressing 35S::bait249-GFP, 35S::bait249R-GFP, 35S::bait249NF_Tand-GFP and 35S::bait249NF-GFP. The increased absorbance at 1616 and at 1680 (black arrows) values indicate the presence of β-sheet aggregates.

FIG. 9. (a) Phenotype of 35S::bait249R-GFP and 35S::bait249NF_Tand-GFP Arabidopsis seedlings compared to Col-0 grown vertically in vitro for 8 days under long day photoperiod and in soil for 1.5 months. Quantification of roots and hypocotyls lengths on an average of 50 8 D.A.S. seedlings per line is also represented. (b) Brazzinazole resistance dose response assay for 35S::bait249R-GFP and 35S::bait249NF_Tand-GFP Arabidopsis 4 D.A.S. seedlings lines compared to Col-0 and triple GSKs group II T-DNA mutant (trGSKsII_k.o.). Corresponding quantification of hypocotyls lengths on an average of 50 seedlings per line is represented in the graph.

Figure 10:
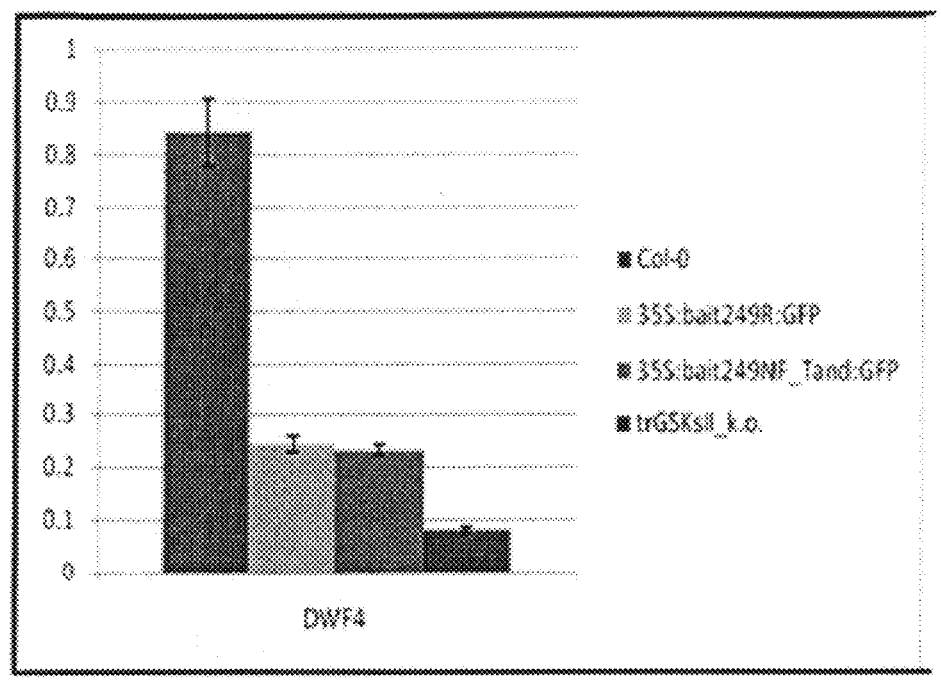
Figure 10:
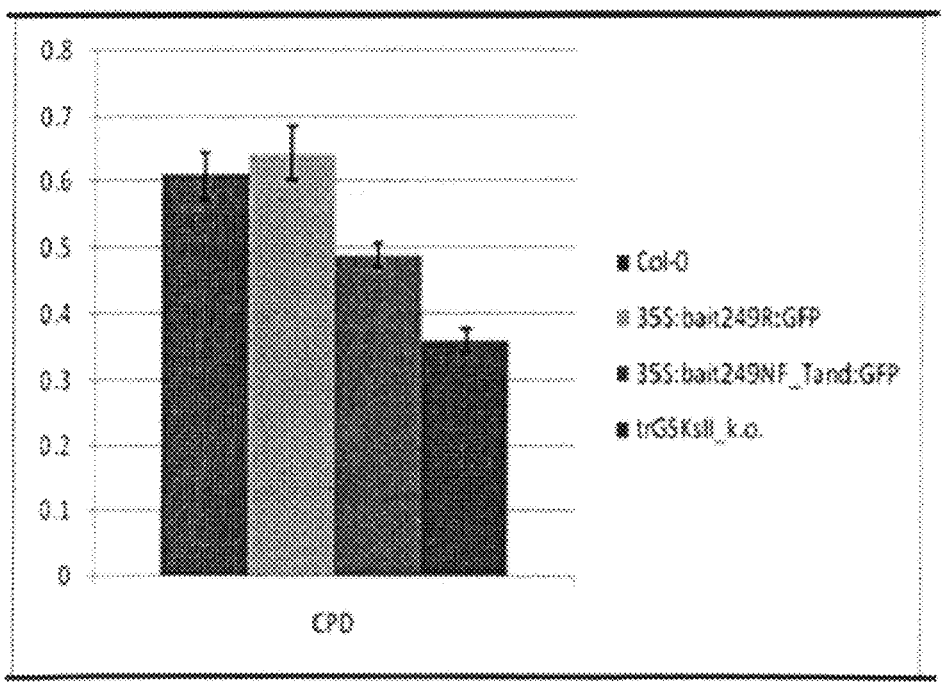
Figure 10:
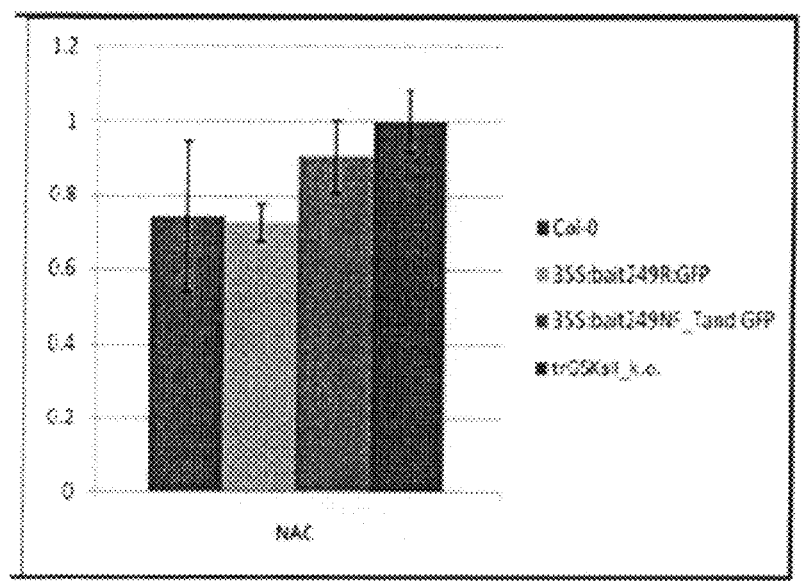

FIG. 10 a) Relative expression levels of the BR-biosynthetic genes DWF4 and CPD and of the gene for the BR-responsive NAC transcription factor (At5g46590) in 8 D.O. Arabidopsis seedlings grown in vitro under long day conditions. b) Chaperone genes (HSP70, HSP90-1, HSP101, HSC70-1, HSC70-2 and HSC70-3) expression levels measured in the same experimental conditions. In each case the mRNA amount was normalized to the level of CDKA1 as reference gene.

Figure 11:
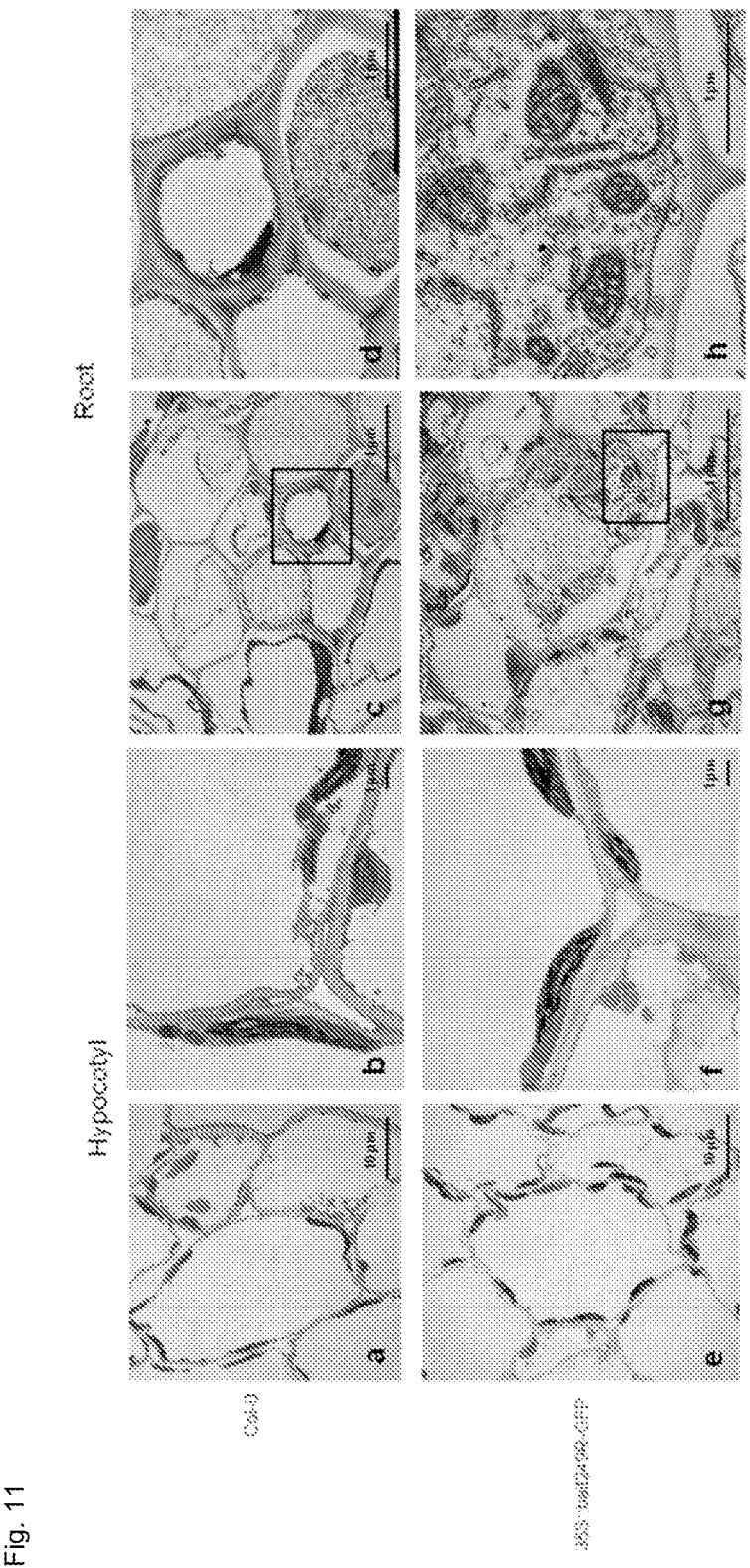

FIG. 11. TEM ultrastructural evaluation of 35S::bait249R-GFP cytotoxicity in Arabidopsis plants. A low magnification comparison between hypocotyls and root cells in Col-0 (a,c) and the mutant (e,g) is showed. High magnification micrographs of the same areas in Col-0 (b,d) and mutant (f,h). Size bars are indicated.

Figure 12:
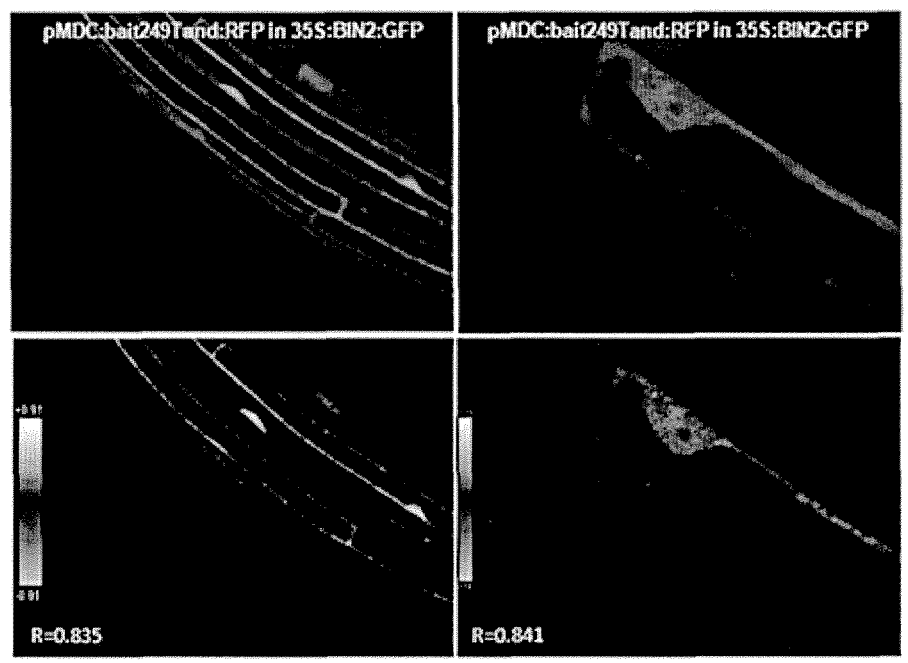

FIG. 12. Upper panel: CSM images of 8 D.A.S. Arabidopsis seedlings expressing 35S::BIN2-GFP and pMDC::bait249NF_Tand_RFP after 24 hours of induction. In the bottom panel: corresponding images representing co-localization quantification performed by ImageJ MBF software. Mander's overlap coefficients (0<R<1) for each picture are indicated.

AIMS AND DETAILED DESCRIPTION OF THE INVENTION

This application is a continuation in part of copending U.S. application Ser. No. 12/214,761 filed Jun. 20, 2008 (published as US20090012275).

In the present invention we have developed a process for down-regulating the biological function of a protein through the use of interferor molecules that have a specificity for a target protein. Upon contact with a target protein a co-aggregation occurs between the interferor molecule and the target. The aggregation withdraws the target from its soluble environment and results in a functional knock-down of the target protein.

Thus in one embodiment the invention provides a method for down-regulating the biological function of a protein comprising contacting said protein with a non-naturally occurring molecule comprising at least one self-association region isolated from said protein.

In another embodiment the invention provides a method for down-regulating the biological function of a protein comprising contacting said protein with a non-naturally occurring molecule consisting of at least one self-association region isolated from said protein.

In yet another embodiment the invention provides a method for down-regulating the biological function of a protein comprising contacting said protein with a non-naturally occurring molecule comprising at least one self-association region isolated from said protein wherein said self-association domain is fused to a moiety that prevents aggregation of said self-association region.

In yet another embodiment the invention provides a method for down-regulating the biological function of a protein comprising contacting said protein with a non-naturally occurring molecule consisting of at least one self-association region isolated from said protein wherein said self-association domain is fused to a moiety that prevents aggregation of said self-association region.

In yet another embodiment the invention provides a method for down-regulating the biological function of a protein in a plant or plant cell, the method comprising: i) contacting said protein with a non-naturally occurring molecule, wherein said protein comprises a first β-aggregating region, said non-naturally occurring molecule comprises a second β-aggregating region, and said first and second β-aggregating regions are identical, ii) intermolecular beta-aggregation occurs between the protein and the non-naturally occurring molecule, iii) the non-naturally occurring molecule is a polypeptide, and iv) said biological function is down-regulated, wherein the contacting between the protein and the non-naturally occurring molecule is produced by expression of said non-naturally occurring molecule in said plant or plant cell.

In yet another embodiment the invention provides a method for down-regulating the biological function of a protein comprising contacting said protein with a non-naturally occurring molecule which comprises part A and part B wherein i) part A is a peptide, or a protein domain or an agarose bead preventing aggregation of part B and ii) part B which comprises at least 1 self-association region consisting of at least 3 contiguous amino acids and wherein said region is isolated from said protein which function is to be down-regulated with, and wherein a linker is optionally present between parts A and B.

In yet another embodiment the invention provides a method for down-regulating the function of a protein comprising contacting said protein with a non-naturally occurring molecule which comprises part A and part B wherein i) part A is a peptide, or a protein domain or an agarose bead preventing aggregation of part B so that part B is in direct contact with the solvent wherein said molecule and said protein are present and ii) part B which comprises at least 1 self-association region wherein said region consists of at least 3 contiguous amino acids and wherein said region is isolated from said protein which function is to be down-regulated with, and wherein a linker is optionally present between parts A and B.

In particular embodiments the self association region (or beta-aggregation region) consists of at least 4, at least 5, at least 6, at least 7, at least 8 or at least 9 contiguous amino acids wherein said region is isolated from a target protein.

In another embodiment part B of the non-naturally occurring molecule comprises at least 2 self-association regions wherein at least one of said regions is derived from said protein which function is to be interfered with.

The term 'non-naturally occurring molecule' refers to the fact that such an interferor molecule is man made. For instance, when an interferor molecule is polypeptide (id est both part A and B are peptides) such polypeptide is designed by isolating part B from a target protein (id est the self association region) and by coupling said part B to a part A which can be derived (i) from another protein or (ii) from the same target protein in which case said part A is not present immediately adjacent to part B. In still other words the self-association region derived from the target fused to a moiety (when the interferor is a polypeptide said moiety is also a polypeptide) that prevents the aggregation of the self-association region is different from a naturally occurring fusion between part A and B by at least one natural amino acid. Typically, such interferor molecule will not exist as a contiguous polypeptide in a protein encoded by a gene in a non-recombinant genome. In the present invention it is understood that the 'non-naturally occurring molecule' or more specifically the 'non-naturally occurring polypeptide' can be encoded by an 'artificial gene'.

It should be clear that interferor molecules can be designed in a modular fashion, by introducing repetition and changing the order of the parts A and B. A non-limiting list of the following combinations is: an interferor with the A-B—structure, an interferor with the B-A—structure, an interferor with the A-B-A—structure, an interferor with the B-A-B—structure, an interferor with the A'-B-A" structure and an interferor with the B'-A-B" structure wherein a linker (spacer) is optionally present between parts A, A', A" and B, B', B". A, A' and A" are different of similar moieties (e.g. different peptide sequences). B, B' and B" are different or similar self association sequences (e.g. B is a self-association sequence derived from the target protein and B' is a synthetic self-association sequence). In the context of the present invention a 'self association region' is herein equivalent with the wording a 'beta-aggregation region'.

In still other words the invention provides a method for down-regulating the biological function of a protein comprising contacting said protein with a molecule comprising at least one self-association region isolated from said protein wherein said self-association region is fused to a moiety that prevents aggregation of said self-association region so that said self-association region is in direct contact with the solvent wherein said molecule and said protein are present. From the above it should be clear that said 'moiety' is equivalent with the term part A and part B is equivalent with the wording 'at least one self association region'.

The wording 'down-regulating the function of a protein' means that the normal biological activity of a protein is reduced (inhibited, down-regulated, reduced and disrupted are equivalent words here) or that the protein is withdrawn from its normal biological environment (e.g. a protein which is a normal resident of the endoplasmic reticulum is not present through down-regulation of its function). Thus, by applying the method of the invention the function of a protein is disrupted through an aggregation of said protein by contacting said protein with the non-natural molecule of the present invention. Said non-natural molecule is herein designated as 'the interferor' or the 'interferor molecule'. Aggregation refers to the fact that a protein which is normally soluble is changed into an insoluble protein or an aggregated protein in its normal biological environment through direct contact or binding with the interferor. The wording 'down-regulating the function of a protein' can also be interchanged by the wording 'knocking down the function of a protein' or 'negatively interfering with the function of a protein'. The down-regulation of the function of a protein can also mean that a protein is not present anymore in a soluble form in the cell or that a protein is not present anymore in a soluble form in its normal biological environment (e.g. (sub)-cellular or extra-cellular localization). In addition, it can also mean that the aggregated protein is degraded through the natural clearance mechanisms of the cell and is no longer detectable in soluble or insoluble form. In addition, it can also mean that a transmembrane receptor protein cannot bind its normal ligand anymore through interferor induced aggregation of said transmembrane protein. Thus the down-regulation of the function of a protein can also mean that a protein which is a normal resident of e.g. the mitochondria is not present there anymore through the method of protein interference. In a particular embodiment the 'down-regulation of the function of a protein' or 'the negative interference with the function of a protein' or 'knocking down the function of a protein' is at least a 20%, at least a 30%, at least a 40%, at least a 50%, at least a 60%, at least a 70%, at least a 80%, at least a 90%, at least a 95% or even a 100% loss of function as compared to the normal (100%) function of the protein.

The function of a protein or the lack of presence of a protein in its normal biological environment (localization) can conveniently be determined by methods known in the art. For example, depending on the target protein of interest, the function can be determined by measuring the reduced enzymatic activity. The reduced presence of a protein in its normal biological localization can for example be measured by the lack of formation of a complex, the lack of the occurrence of a target protein in a sub-cellular compartment, the presence of the target protein in soluble form, the presence of the target protein in an aggregated (insoluble is an equivalent term here) form. Alternatively, the effect of the down-regulation of a target protein can be measured in a cellular assay (e.g. loss or gain of growth, loss or gain of invasion, loss or gain of proteolytic activity).

In a particular embodiment such normal biological activity (or normal function or normal localization) of a protein can be interfered with intracellularly or extracellularly. 'Intracellularly' refers to the localization of a protein inside the cell of an organism or host (e.g. the cytoplasm, the mitochondria, the lysosome, the vacuole, the nucleus, the chloroplast, the endoplasmic reticulum (ER), the cellular membrane, the mitochondrial membrane, the chloroplast membrane, ... ). 'Extracellularly' not only refers to the localization of a protein in the extracellular medium of the cell but also refers to proteins which contact the extracellular medium such as a membrane-anchored proteins, a transmembrane protein etc. Non-limiting examples of extracellular proteins are secreted proteins (e.g. proteases, antibodies and cytokines present in the blood or plasma) or proteins present in the extracellular matrix (e.g. matrix metalloproteins and transmembrane proteins (e.g. a growth factor receptor)).

Cells or hosts which can be targeted with the method of the invention comprise prokaryotic and eukaryotic cells. Non-limiting examples are viruses, bacteria, yeasts, fungi, protozoa, plants and mammals including humans.

It should be clear that the method of down-regulation the biological function of a protein can be used to interfere with the biological function with 1, 2, 3, 4, 5 or even more proteins simultaneously. Particularly since part B comprises at least one self-association region, part B can for example comprise different self-association regions each specific for a different protein. The interferor used for interference with the biological function of at least one target protein is not naturally present in nature and can be made through chemical synthesis or through recombinant protein expression or through a combination of the latter.

Thus an interferor molecule comprises at least one self-association region (thus part B comprises at least one self-association region). A 'self-association region' is herein defined as a contiguous sequence of amino acids that has a high tendency to form a tight molecular assembly with identical or very closely related sequences. The wording 'has a high tendency to form a tight molecular assembly' can also be construed as 'has a high affinity'. Affinity is usually translated into values of dissociation (Kd-values). Kd-values between interferor and target proteins are typically lying between micromolar and nanomolar ranges, but can be sub-nanomolar or supra-micromolar. Examples of self-association regions are intermolecular beta sheet regions, alpha-helical elements, hairpin loops, transmembrane sequences and signal sequences. In a particular embodiment at least one self-association region is present in part B. In another particular embodiment at least two self-association regions are present in part B. In another particular embodiment 3, 4, 5, 6 or more self-association regions are present in part B. Said self-association regions can be interconnected by a linker region (e.g. a spacer of about 2 to about 4 amino acids). One (or at least one) self-association region present in part B is derived from a target protein. In a particular embodiment 2, 3, 4, 5, 6 or more self-association regions in part B are derived from a target protein. In another particular embodiment 2, 3, 4, 5, 6 or more self-association regions in part B are derived from more than 1 target protein. In another particular embodiment the at least two self-association regions present in part B are derived from the same target protein. The target protein is defined herein as the protein with which one wants to interfere with its function. Thus, in order to make part B specific for at least one protein at least one self-association region in part B should be 'derived from' the target protein or at least one self-association region should be present in said target protein. 'Derived from' means that at least one contiguous self-associating region should be identical or homologous in amino acid sequence to a contiguous region of said target protein. In a preferred embodiment, said at least one self-associating region is at least 60%, at least 65%, at least 70%, at least 75%, at least 80%, at least 85%, at least 90%, at least 95% or at least 100% identical to the self-association region present in said target protein region.

It is preferred that the length of a self-association region consists of at least 3 contiguous amino acids. In a preferred embodiment said region consists of about 3 to about 30 amino acids. In another preferred embodiment said region consists of about 3 to about 25 amino acids. In a particularly preferred embodiment said region consists of about 5 to about 20 amino acids.

Self-association regions present in part B of the interferor molecule also can be determined and isolated from proteins other than the target protein and said self-association regions are coupled with at least one self-association region derived from the target protein, optionally with a spacer (or linker) between said self-association regions. For example, self-association regions that can be used can be derived from self-association regions of proteins which do not normally occur in the host in which the down-regulation of the biological function of a target protein is performed (thus some self-association regions in part B can be taken from an unrelated organism). The nature of the self-association regions determine the level of inhibition (id est the strength of inhibition) of a target protein through induced aggregation. More than one self-association region can be used from a target protein in an interferor molecule but also synthetic self-association regions or self-association regions derived from a different target protein can be used in combination with one or more self-association regions from a target protein.

In a particular embodiment such self-association regions consist of a synthetic sequence which is not derived from existing proteins and hence does not occur in nature. Examples of such synthetic self association regions are described in Lopez de la Paz M. et al (2002) PNAS 99, 25, p. 16053, table 1.

If at least one self-association region (id est the part B of the interferor molecule) has a hydrophobic character (because of its aggregation inducing properties) it is preferably fused (or linked or coupled which are equivalent terms) to a moiety (id est part A of the interferor molecule) that prevents aggregation of said self-association region and exposes said self-association region in direct contact with the solvent in which the interferor is present. As such, in certain embodiments part A has a solubilizing function to keep part B in solution. In such embodiments said part A is for example a peptide, a protein domain, a protein (preferably different from the target protein, see example 2), a glycosylation structure, a (hydrophilic) chemical group or a cyclodextrine or derivative thereof. In certain other embodiments said part A is an agarose bead, a latex bead, a cellulose bead, a magnetic bead, a silica bead, a polyacrylamide bead, a microsphere, a glass bead or any solid support (e.g. polystyrene, plastic, nitrocellulose membrane, glass).

In the interferor molecules part B and part A may be optionally linked (or coupled) by means of a linker region (a spacer is an equivalent word). Said linker region can for instance be an unnatural linker made by chemical synthesis (e.g. a flexible linker such as a hydroxy-substituted alkane chain, dextran, polyethylene glycol or the linker can also consist of amino acid homologues) or said linker can exist of natural amino acids such as a poly(threonine) or poly(serine). Preferentially when the linker comprises amino acids, the length of said linker region is between about 3 and about 15 amino acids, more preferably between about 5 and about 10 amino acids. Often a flexible linker can be chosen but it is envisaged that a stiff linker will also work. Flexible linker sequences can be taken from nature, mostly such regions connect domains in naturally occurring proteins, such as the linker between the SH2 and SH3 domains src tyrosine kinase or the linker between the BRCT domains of BRCA1.

The term 'contacting' refers to the process in which the interferor and the target protein interact. In one form the interferor is added (e.g. interferor is present at a particular concentration in a solution) to a sample comprising the target protein. In another form the interferor molecule is injected into an organism comprising the target protein. Contacting can for example also be carried out through the process of transformation of a cell comprising the target protein, e.g. an isolated cell, e.g. in cell culture, a unicellular microorganism or a cell or a plurality of cells within a multicellular organism. Transformation implies that the interferor molecule is introduced in a host (e.g. a cell) through commonly known transfection or transformation methods (e.g. by gene transfer techniques including calcium phosphate, DEAE-dextran, electroporation, microinjection, viral methods, the use of cationic liposomes (see for example Feigner, P. L. et al. (1987), Proc. Natl. Acad. Sci USA 84, 7413), commercially available cationic lipid formulations e.g. Tfx 50 (Promega) or Lipofectamin2000 (Life Technologies), particle bombardment, etc.). The interferor molecule may be encoded by a recombinant vector (e.g. a plasmid, cosmid, viral vector) and can be synthesized inside a host. In an alternative embodiment the interferor molecule can be introduced into a cell through carrier-mediated delivery, e.g. by liposomal carriers or nanoparticles or by injection. In yet another alternative embodiment the interferor molecule can enter a cell through a sequence which mediates cell penetration (or cell translocation). In the latter case the interferor molecule is further modified through the recombinant or synthetic attachment of a cell penetration sequence. Thus, the interferor molecule (e.g. as a polypeptide) may be further fused or chemically coupled to a sequence facilitating transduction of the fusion or chemical coupled proteins into prokaryotic or eukaryotic cells. Sequences facilitating protein transduction are known to the person skilled in the art and include, but are not limited to Protein Transduction Domains. Preferably, said sequence is selected from the group comprising of the HIV TAT protein, a polyarginine sequence, penetratin and pep-1. Still other commonly used cell-permeable peptides (both natural and artificial peptides) are disclosed in Joliot A. and Prochiantz A. (2004) Nature Cell Biol. 6 (3) 189-193.

In a particular embodiment the interferor essentially consists of amino acids. In some embodiments the sequences of parts A and B from the interferor molecule are derived from the same target protein. In other embodiments the interferor is a molecule meaning that the sequences from parts A and B are derived from different proteins, e.g. part A is derived from one protein and at least one aggregation region of part B is derived from the target protein. A "Polypeptide" refers to a polymer in which the monomers are amino acids and are joined together through amide bonds, alternatively referred to as a peptide. When the amino acids are alpha-amino acids, either the L-optical isomer or the D-optical isomer can be used. Additionally, unnatural amino acids, for example, beta-alanine, phenylglycine and homoarginine are also included. Commonly encountered amino acids that are not gene-encoded may also be used in the present invention. All or part of the amino acids used in the interferors may be either the D- or L-isomer. In addition, other peptidomimetics are also useful in the present invention. We specifically refer and incorporate herein the review of the development and use of peptidomimetics as antagonists for protein-protein interactions from Sillerud L O and Larson R S (2005) *Curr Protein Pept Sci.* 6(2):151-69. Furthermore, D-amino acids can be added to the peptide sequence to stabilize turn features (especially in the case of glycine). In another approach alpha, beta, gamma or delta turn mimics (such as alpha, beta, gamma, or delta di-peptides can be employed to mimic structural motifs and turn features in a peptide and simultaneously provide stability from proteolysis and enhance other properties such as, for example, conformational stability and solubility.

Isolation of a Self Association Region (or a Beta-Aggregation Region) from a Target Protein:

Self-association sequences are often hydrophobic but this is not always the case. For example, the self-associating regions of the yeast prions are rather polar. In fact cross-beta aggregation of an amino acid region derived from a polypeptide or protein can be initiated when (1) it has a high hydrophobicity, (2) it has a good β-sheet propensity, (3) it has a low net charge and (4) it is solvent-exposed. Thus, self-association protein regions ('segment' is an equivalent term for 'region') are most often buried in the folded state and are not exposed to the solvent. The latter is confirmed by the experimental finding that in many globular proteins, aggregation occurs during refolding or under conditions in which denatured or partially folded states are significantly populated, i.e. at high concentration or as a result of destabilizing conditions or mutations.

Based on these findings computer algorithms were developed that are able to predict self-association regions (".beta.-aggregating stretches or segments or regions" is an equivalent wording) in proteins. One such algorithm, TANGO, is based on a statistical mechanics algorithm that considers the three physico-chemical parameters described above but also considers competition between different structural conformations: beta-turn, alpha-helix, beta-sheet aggregates and the folded state (Fernandez-Escamilla, A M et al (2004) Nat. Biotechnol. 22, 1302-1306, especially the Methods section on pages 1305 and 1306 are herein specifically incorporated by reference and also the Supplementary Notes 1 and 2 of the same article for further details on the methods and the data sets used for the calibration and the testing of the TANGO algorithm). Thus, self-association regions present in target proteins are obtainable by computer algorithms such as TANGO. Self-association regions are often buried inside the core of the target proteins[10], effectively shielding the peptide from intermolecular association by an energy barrier corresponding to the stability of the target proteins[11]. In its normal environment (e.g. cytoplasm, extracellular matrix) the target protein has assistance from molecular chaperones that assist the protein in keeping its functional, monomeric form[12]. The model used by the TANGO algorithm[6] is designed to predict beta-aggregation in peptides and proteins and consists of a phase-space encompassing the random coil and the native conformations as well as other major conformational states, namely beta-turn, alpha-helix and beta-aggregate. Every segment of a peptide can populate each of these states according to a Boltzmann distribution. Therefore, to predict self-association regions of a peptide, TANGO simply calculates the partition function of the phase-space. To estimate the aggregation tendency of a particular amino acid sequence, the following assumptions are made: (i) in an ordered beta-sheet aggregate, the main secondary structure is the beta-strand. (ii) the regions involved in the aggregation process are fully buried, thus paying full solvation costs and gains, full entropy and optimizing their H-bond potential (that is, the number of H-bonds made in the aggregate is related to the number of donor groups that are compensated by acceptors. An excess of donors or acceptors remains unsatisfied). (iii) complementary charges in the selected window establish favorable electrostatic interactions, and overall net charge of the peptide inside but also outside the window disfavors aggregation. TANGO can be accessed on the World Wide Web at tango.embl.de. The zyggregator algorithm is another example (Pawar A P et al (2005) J. Mol. Biol. 350, 379-392). These algorithms identify aggregation prone sequences by comparing the aggregation propensity score of a given amino acid sequence with an average propensity calculated from a set of sequences of similar length.

In the present invention we estimate that a self-association region identified within a target protein with a TANGO score of 5% corresponds to an aggregation risk in vitro of 95%[6]. We have calculated that 85% of proteins from the human proteome that are not related to disease have at least one region with a TANGO score above the experimentally determined threshold of 5%. This shows that although more than 85% of the human proteins contain at least one single self-association region that aggregation is prevented because of the normal stability of the protein and the assistance from the chaperone machinery. The present invention isolates these self-association regions from target proteins for the preparation of interferor molecules which are used for the specific induction of protein aggregation. The B-part of the interferor molecules comprises at least 1 aggregation region and at least one aggregation region is derived from a target protein. It is possible to control the strength of the protein interference (the strength of protein interference is for example the % of loss of biological function of a target protein when said protein or cell comprising said protein is contacted with a specific interferor molecule) through the incorporation of more than one aggregation region of a target protein in the B-part of the interferor molecule. Indeed, aggregation regions derived from a target protein with a low TANGO score (typically between 5% to about 20%) can be repeated in the B-part of the interferor to 2, 3, 4 or more aggregation regions. As an alternative embodiment 1, 2 or 3 or 4 or more different aggregation regions with a low TANGO score derived from the same protein can be incorporated into the B-part of the interferor. As another alternative embodiment 1, 2, 3, 4 or more synthetic aggregation regions (thus not derived from the target protein) can be combined with 1, 2, 3, 4, or more aggregation regions derived from the target protein into the B-part to enhance the down-regulation of a target protein with a low TANGO score.

Thus in another embodiment the invention provides a non-naturally occurring molecule capable of aggregating a target protein. In a particular embodiment said non-naturally molecule is proteinaceous in nature. Proteinaceous means that the molecule comprises L-amino acids or D-amino acids or a mixture of L- and D-amino acids or a combination of natural amino acids and peptidomimetics.

In yet another embodiment the invention provides a non-naturally occurring molecule comprising at least one self-association region isolated from a protein domain capable of being soluble in water wherein said self-association region is fused to a moiety that prevents aggregation of said self-association region.

In yet another embodiment the invention provides a non-naturally occurring molecule comprising at least one self-association region isolated from a protein domain capable of being soluble in water wherein said self-association region is fused to a moiety that prevents aggregation of said self-association region so that said self-association region is in direct contact with the solvent wherein it is present.

In yet another embodiment the invention provides a non-naturally occurring molecule consisting of at least one self-association region isolated from a protein domain capable of being soluble in water wherein said self-association region is fused to a moiety that prevents aggregation of said self-association region.

In yet another embodiment the invention provides a non-naturally occurring molecule consisting of at least one self-association region isolated from a protein domain capable of being soluble in water wherein said self-association region is fused to a moiety that prevents aggregation of said self-association region so that said self-association region is in direct contact with the solvent wherein it is present.

In a particular embodiment such a moiety is for example a peptide, an agarose bead, a protein domain or a protein. In another particular embodiment said non-naturally occurring molecule comprises at least two self-association regions of which at least one self-association region is derived from a target protein.

In other words the invention provides a non-naturally occurring molecule, which comprises part A and part B wherein i) part A comprises a region, such as a peptide, protein domain, protein or agarose bead preventing the aggregation of part B, and ii) part B which comprises at least 1 self-association region wherein said region consists of at least 3 contiguous amino acids and wherein said region is isolated from said protein which function is to be interfered with, and wherein a linker is optionally present between parts A and B.

In still other words the invention provides a non-naturally occurring molecule which comprises part A and part B wherein i) part A comprises a region, such as a peptide, protein domain or agarose bead preventing the aggregation of part B, and ii) part B which comprises at least 1 self-association region consisting of at least 3 contiguous amino acids and wherein at least one self-association region is isolated from a protein which function is to be interfered with and wherein said region is isolated from a domain from said protein which is capable of being soluble in water, and wherein a linker is optionally present between parts A and B, and wherein part B is in direct contact to the environment wherein said molecule and said protein are present.

In still other words the invention provides a non-naturally occurring molecule which comprises part A and part B wherein i) part A comprises a region, such as a peptide, protein domain or agarose bead preventing the aggregation of part B, and ii) part B which consists of at least 1 self-association region consisting of at least 3 contiguous amino acids and wherein said at least one self-association region is isolated from a protein which function is to be interfered with and wherein said region is derived from a domain from said protein which is capable of being soluble in water, and wherein a linker is optionally present between parts A and B, and wherein part B is in direct contact to the environment wherein said molecule and said protein are present.

In yet another embodiment the invention provides an artificial gene comprising the following operably linked DNA elements: a) a plant expressible promoter b) a DNA region encoding for at least one beta-aggregation region isolated from a target protein and c) a 3' end region comprising transcription termination and polyadenylation signals functioning in cells of said plant.

In yet another embodiment the invention provides an artificial gene comprising the following operably linked DNA elements: a) a plant expressible promoter b) a DNA region encoding for at least one beta-aggregation region isolated from a target protein wherein said beta-aggregation region consists of at least 3 contiguous amino acids and c) a 3' end region comprising transcription termination and polyadenylation signals functioning in cells of said plant.

In yet another embodiment the invention provides an artificial gene comprising the following operably linked DNA elements: a) a plant expressible promoter b) a DNA region encoding for at least one beta-aggregation region isolated from a target protein wherein said beta-aggregation region is fused to a moiety to prevent aggregation of said beta-aggregation region and c) a 3' end region comprising transcription termination and polyadenylation signals functioning in cells of said plant.

The wording 'isolated (or derived form) from a domain from said protein which is capable of being soluble in water' means that a self association region is a contiguous amino acid sequence isolated from a soluble domain of a protein. The latter also means that self-association regions derived from transmembrane regions or self-association regions derived from signal sequences are specifically excluded in the claim scope of these interferor molecule products in such embodiments.

In the present invention the at least one self-association region of the interferor molecule (id est part B of the interferor molecule), is 'in direct contact' with the environment (e.g. solvent, cytosol) in which said interferor molecule is present. The importance of this is clarified further. In globular proteins self-association sequences (also designated as 'aggregation nucleating regions') are generally buried in the hydrophobic core of the globular protein and as such kept protected from the solvent by a dense network of cooperative interactions stabilizing the native state. Hence, under normal circumstances there is no 'direct contact' between said self-association region and the environment (for example the solvent). Only when the protein is unfolded, for example when it is synthesized on the ribosome or destabilized by mutation, change of temperature, pH or loss of a specific chaperone, thereby favoring the unfolded state, will it expose its self-association regions to the environment. Self-association regions are normally buried inside proteins (in order to prevent aggregation) and in the non-natural interferor molecule said self-association regions have been isolated and exposed to the environment by linking said regions to a moiety that prevents aggregation (id est part A of the interferor molecule). In still other words, the non-naturally interferor molecule does not fold into a globular structure and therefore the at least one self-association region (id est part B) in the non-natural interferor molecule is in direct contact with the solvent in which said interferor molecule is present. Hence, 'in direct contact' refers to the opposite of 'being buried and kept protected from'.

In a specific embodiment the interferor molecules that comprise at least one self-association region derived from a soluble protein domain are polypeptides.

In another specific embodiment the invention provides a recombinant vector comprising a polynucleotide encoding such interferor molecules.

In another specific embodiment the interferor molecules of the invention are used as a medicament.

In yet another embodiment the method of protein interference of the invention may be used for determining the function of a protein in a cell or an organism being capable of mediating protein interference. The cell can be a prokaryotic cell or can be a eukaryotic cell or can be a cell line, e.g. a plant cell or an animal cell, such as a mammalian cell, e.g. an embryonic cell, a pluripotent stem cell, a tumor cell, e.g. a teratocarcinoma cell or a virus-infected cell. The organism is preferably a eukaryotic organism, e.g. a plant or an animal, such as a mammal. In a particular embodiment a plant cell is used. In yet another particular embodiment a plant protoplast is used.

The target protein to which the interferor molecule of the invention is directed may be associated with a pathological condition. For example, the protein may be a pathogen-associated protein, e.g. a viral protein, a tumor-associated protein or an autoimmune disease-associated protein. The target protein may also be a heterologous gene expressed in a recombinant cell or a genetically altered organism. By inhibiting the function of such a protein valuable information and benefits in the agricultural field or in the medicine or veterinary medicine field may be obtained. In a particularly preferred embodiment the method of the invention is used with an eukaryotic cell or a eukaryotic non-human organism exhibiting a target protein-specific knockout phenotype comprising an at least partially deficient expression of at least one endogenous target protein wherein said cell or organism is contacted with at least one interferor molecule capable of inhibiting the function of at least one endogenous target protein or with a vector encoding at least interferor molecule capable of interfering with the function and/or presence of at least one endogenous protein. It should be noted that the present invention also allows a target-specific knockout of several different endogenous proteins due to the specificity of the interferor molecule.

Using the protein based knockout technologies described herein, the expression of an endogenous target protein may be inhibited in a target cell or a target organism. The endogenous protein may be complemented by an exogenous target nucleic acid coding for the target protein or a variant or mutated form of the target protein, e.g. a gene or a cDNA, which may optionally be fused to a further nucleic acid sequence encoding a detectable peptide or polypeptide, e.g. an affinity tag, particularly a multiple affinity tag. Variants or mutated forms of the target protein differ from the endogenous target protein in that they differ from the endogenous protein by amino acid substitutions, insertions and/or deletions of single or multiple amino acids. The variants or mutated forms may have the same biological activity as the endogenous target protein. On the other hand, the variant or mutated target protein may also have a biological activity, which differs from the biological activity of the endogenous target protein, e.g. a partially deleted activity, a completely deleted activity, an enhanced activity etc. The complementation may be accomplished by co-expressing the polypeptide encoded by the exogenous nucleic acid, e.g. a fusion protein comprising the target protein and the affinity tag and the interferor molecule for knocking out the endogenous protein in the target cell. This co-expression may be accomplished by using a suitable expression vector expressing both the polypeptide encoded by the exogenous nucleic acid, e.g. the tag-modified target protein and the interferor molecule or alternatively by using a combination of expression vectors or alternatively the interferor molecule may contact the target cell from the outside of the cell. Proteins and protein complexes which are synthesized de novo in the target cell will contain the exogenous protein, e.g. the modified fusion protein. In order to avoid suppression of the exogenous protein function with the interferor molecule, the exogenous protein must have sufficient amino acid differences in the aggregation region that is selected for the design of the interferor molecule. Alternatively, the endogenous target protein may be complemented by corresponding proteins from other species, or the endogenous target protein may be complemented by a splice form of said target protein. The combination of knockout of an endogenous protein and rescue by using mutated, e.g. partially deleted exogenous target has advantages compared to the use of a knockout cell. Further, this method is particularly suitable for identifying functional domains of the target protein.

In a further preferred embodiment a comparison, e.g. of gene expression profiles and/or proteomes and/or phenotypic characteristics of at least two cells or organisms is carried out. These organisms are selected from: (i) a control cell or control organism without target protein inhibition, (ii) a cell or organism with target protein inhibition and (iii) a cell or organism with target protein inhibition plus target protein complementation by an exogenous target nucleic acid encoding said target protein.

The methods of the invention are also suitable in a procedure for identifying and/or characterizing pharmacological agents, e.g. identifying new pharmacological agents from a collection of test substances and/or characterizing mechanisms of action and/or side effects of known pharmacological agents. Thus, the present invention also relates to a system for identifying and/or characterizing pharmacological agents acting on at least one target protein comprising: (a) a eukaryotic cell or a eukaryotic non-human organism capable of expressing at least one endogenous target gene coding for said target protein, (b) at least one interferor molecule capable of inhibiting the expression of said at least one endogenous target gene, and (c) a test substance or a collection of test substances wherein pharmacological properties of said test substance or said collection are to be identified and/or characterized. Further, the system as described above preferably comprises: (d) at least one exogenous target nucleic acid coding for the target protein or a variant or mutated form or splice form of the target protein wherein said exogenous target protein differs from the endogenous target protein on the amino acid level of the aggregation regions such that the function of the exogenous target protein is substantially less inhibited by the interferor molecule than the expression of the endogenous protein.

In addition, the invention also comprises cells and organisms comprising an interferor molecule. An organism can for example be a transgenic plant which carries the genetic information that encodes an interferor. Such a transgenic plant is in a preferred embodiment a silenced plant (id est in which a particular target protein is down-regulated because of the presence of a specific interferor in a sub-set of cells or organs or organelles (e.g. chloroplasts) or present in all cells and organs of said plant). Cells comprising an interferor can be produced by contacting said cells or by electroporation of said cells (e.g. plant cells, plant protoplasts or plant seeds) with a particular interferor molecule. In a particular embodiment cells comprising an interferor are generated through transfection (or transformation) wherein the interferor is encoded by a recombinant expression vector such as a plasmid or a viral vector.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "a target protein" means one target protein or more than one target protein.

As used herein, the term "about" refers to a quantity, level, value, dimension, size, or amount that varies by as much as 30%, preferably by as much as 20%, and more preferably by as much as 10% to a reference quantity, level, value, dimension, size, or amount.

"Bifunctional crosslinking reagent" means a reagent containing two reactive groups, the reagent thereby having the ability to covalently link two elements such as part A and part B of the interferor molecule. The reactive groups in a crosslinking reagent typically belong to the classes of functional groups including succinimidyl esters, maleimides and haloacetamides such as iodoacetamides. Throughout this specification, unless the context requires otherwise, the words "comprise", "comprises" and "comprising" will be understood to imply the inclusion of a stated step or element or group of steps or elements but not the exclusion of any other step or element or group of steps or elements.

By "expression vector" or "recombinant vector" is meant any autonomous genetic element capable of directing the synthesis of an interferor molecule encoded by the vector. Such expression vectors are known to practitioners in the art.

By "derivative" is meant an interferor molecule that has been derived from the basic sequence by modification, for example by conjugation or complexing with other chemical moieties (e.g. pegylation) or by post-translational modification techniques as would be understood in the art. The term "derivative" also includes within its scope alterations that have been made to a parent sequence including additions, or deletions that provide for functionally equivalent molecules.

By "effective amount", in the context of modulating an activity or of treating or preventing a condition is meant the administration of that amount of an interferor molecule to an individual in need of such modulation, treatment or prophylaxis, either in a single dose or as part of a series, that is effective for modulation of that effect or for treatment or prophylaxis of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

By "isolated" is meant material that is substantially or essentially free from components that normally accompany it in its native state. For example, an "isolated polypeptide", as used herein, refers to a polypeptide, which has been purified from the sequences which flank it in a naturally-occurring state, e.g., a self-association sequence which has been removed from the sequences that are normally adjacent to said sequence. A self-association sequence (optionally coupled to a moiety that prevents aggregation) can be generated by amino acid chemical synthesis or can be generated by recombinant production.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). An oligonucleotide is typically rather short in length, generally from about 10 to 30 nucleotides, but the term can refer to molecules of any length, although the term "polynucleotide" or "nucleic acid" is typically used for large oligonucleotides. The term "polynucleotide" or "nucleic acid" as used herein designates mRNA, RNA, cRNA, cDNA or DNA. The term typically refers to oligonucleotides greater than 30 nucleotides in length.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "agronomically acceptable carrier" is meant a solid or liquid filler, diluent or encapsulating substance that can be safely used in topical or systemic administration of an interferor molecule to a plant, plant seed, plant cell or plant protoplast.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

By "recombinant polypeptide" is meant a polypeptide made using recombinant techniques, i.e., through the expression of a recombinant or synthetic polynucleotide. When the chimeric polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. "Similarity" refers to the percentage number of amino acids that are identical or constitute conservative substitutions. Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

The term "transformation" means alteration of the genotype of an organism, for example a bacterium, yeast or plant, by the introduction of a foreign or endogenous nucleic acid. Vectors for transformation include plasmids, retroviruses and other animal viruses, YACs (yeast artificial chromosome), BACs (bacterial artificial chromosome) and the like. By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In a preferred embodiment, the vector is preferably a viral or viral-derived vector, which is operably functional in animal and preferably mammalian cells. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

In the present invention a "plant expressible promoter" comprises regulatory elements, which mediate the expression of a coding sequence segment in plant cells. For expression in plants, the nucleic acid molecule must be linked operably to or comprise a suitable promoter which expresses the gene at the right point in time and with the required spatial expression pattern. For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500, 0000 transcripts per cell. Conversely, a "strong promoter" drives expression of a coding sequence at high level, or at about 1/10 transcripts to about 1/100 transcripts to about 1/1000 transcripts per cell. Generally, by "medium strength promoter" is intended a promoter that drives expression of a coding sequence at a lower level than a strong promoter, in particular at a level that is in all instances below that obtained when under the control of a 35S CaMV promoter.

The term "operably linked" as used herein refers to a functional linkage between the promoter sequence and the gene of interest, such that the promoter sequence is able to initiate transcription of the gene of interest.

A "constitutive promoter" refers to a promoter that is transcriptionally active during most, but not necessarily all, phases of growth and development and under most environmental conditions, in at least one cell, tissue or organ. An "ubiquitous" promoter is active in substantially all tissues or cells of an organism. A developmentally-regulated promoter is active during certain developmental stages or in parts of the plant that undergo developmental changes. An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens. An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific". A seed-specific promoter is transcriptionally active predominantly in seed tissue, but not necessarily exclusively in seed tissue (in cases of leaky expression). The seed-specific promoter may be active during seed development and/or during germination. The seed specific promoter may be endosperm/aleurone/embryo specific. Examples of seed-specific promoters are given in Qing Qu and Takaiwa (Plant Biotechnol. J. 2, 1 13-125, 2004), which disclosure is incorporated by reference herein as if fully set forth. A green tissue-specific promoter as defined herein is a promoter that is transcriptionally active predominantly in green tissue, substantially to the exclusion of any other parts of a plant, whilst still allowing for any leaky expression in these other plant parts.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention.

A transgenic plant for the purposes of the invention is thus understood as meaning, as above, that the nucleic acids used in the method of the invention (e.g. the artificial genes) are not present in, or originating from, the genome of said plant, or are present in the genome of said plant but not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, heterologous expression of the nucleic acids takes place. Preferred transgenic plants are mentioned herein.

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

The term "increased expression" or "overexpression" as used herein means any form of expression that is additional to the original wild-type expression level. For the purposes of this invention, the original wild-type expression level might also be zero, i.e. absence of expression or immeasurable expression.

Methods for increasing expression of genes or gene products are well documented in the art and include, for example, overexpression driven by appropriate promoters (as described herein before), the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1 183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 1 16, Freeling and Walbot, Eds., Springer, N.Y. (1994).

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1 102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via Agrobacterium-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for Agrobacterium-mediated transformation of rice include well known methods for rice transformation, such as those described in any of the following: European patent application EP1198985, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming Agrobacterium tumefaciens, for example pBin19 (Bevan et al (1984) Nucl. Acids Res. 12-8711). Agrobacteria transformed by such a vector can then be used in known manner for the transformation of plants, such as plants used as a model, like Arabidopsis or crop plants such as, by way of example, tobacco plants, for example by immersing bruised leaves or chopped leaves in an agrobacterial solution and then culturing them in suitable media. The transformation of plants by means of Agrobacterium tumefaciens is described, for example, by Hofgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of Arabidopsis are treated with agrobacteria and seeds are obtained from the developing plants of which a certain proportion is transformed and thus transgenic [Feldman, K A and Marks M D (1987). Mol Gen Genet 208:1-9; Feldmann K (1992). In: C Koncz, N-H Chua and J Shell, eds, Methods in Arabidopsis Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of Arabidopsis, intact plants under reduced pressure are treated with an agrobacterial suspension [Bechthold, N (1993). CR Acad Sci Paris Life Sci, 316: 1 194-1 199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp.

(e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

The term "expression cassette" refers to any recombinant expression system for the purpose of expressing a nucleic acid sequence of the invention in vitro or in vivo, constitutively or inducibly, in any cell, including, in addition to plant cells, prokaryotic, yeast, fungal, insect or mammalian cells. The term includes linear and circular expression systems. The term includes all vectors. The cassettes can remain episomal or integrate into the host cell genome. The expression cassettes can have the ability to self-replicate or not (i.e., drive only transient expression in a cell). The term includes recombinant expression cassettes that contain only the minimum elements needed for transcription of the recombinant nucleic acid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. The materials, methods, and examples are illustrative only and not intended to be limiting. Other features and advantages of the invention will be apparent from the detailed description and from the claims.

EXAMPLES

Introduction

In order to test the protein interference technology in planta, a cytosolic player of the brassinosteroids (BR) signalling pathway has been selected. BR are steroidal hormones affecting many cellular processes involved in organ growth and plant development including vascular differentiation, senescence, male fertility, flowering, photomorphogenesis, tolerance to biotic and abiotic stresses (Bajguz and Hayat (2009) *Plant Physiol. Biochem* 47(1): 1-8). They are also acting on agronomically interesting traits in crop plants as tiller number, leaf size, and leaf angle (Morinake Y et al (2006) *Plant Physiol* 141(3): 924-31. As an example, the tissue-specific expression of the sterol C-22 hydroxylases, an enzyme controlling BR hormone levels, can enhance the grain filling in rice (Wu C Y et al (2008) *Plant Cell* 20(8): 2130-45).

In *Arabidopsis* BR are perceived by the plasma membrane leucine-rich repeat (LRR) receptor-like kinases (RLK) BRASSINOSTEROID INSENSITIVE 1 (BRI1) which gets activated upon BR binding and associates with BRI1-ASSOCIATED RECEPTOR KINASE 1 (BAK1) inducing sequential transphosphorylation events by which the fully activated BRI1 can further phosphorylate BR-SIGNALING KINASES (BSKs). Then the phosphorylated BSKs are released from the receptor complex and bind to the BRI1 SUPPRESSOR 1 (BSU1) phopsphates, presumably enhancing its activity. Activated BSU1 inhibits Brassinosteroid Insensitive 2 (BIN2) and other kinases belonging to the glycogen synthase kinase-3 (GSK3) family by dephosphorylating its phosphotyrosine residue. Unphopsphorylated BIN2 allows accumulation of active unphosphorylated BRASSINAZOLE RESISTANT1 (BZR1) and BZR2/bri1-EMS-SUPPRESSOR1 (BZR2/BES1) transcription factors in the nucleus. Active BZR1 and BZR2/BES1 bind to genomic DNA to regulate BR-target gene expression, thereby modulating growth and development of plants.

In this pathway a good putative target has been identified in the BR negative regulator BIN2 as we expected that interfering with it by using the protein interference technology would result in agronomically interesting phenotypic changes. To this end the protein aggregation knock out efficiency was correlated with the phenotypic alterations observed by scoring growth parameters as leaf shape and plant height. These parameters have important agronomic effects on crop yield as it has been shown in rice knock-out brassinosteroid signalling mutants which have higher yields in dense planting conditions.

In the present study two main biological questions are addressed; at first whether it is possible to visualize and evaluate the β-aggregation phenomenom in plants, and then if the targeting of a specific protein of interest by aggregating baits is achievable by proving its functional knock-out.

1. Design of BIN2 Interferor Expressing Constructs

Figure 1B:
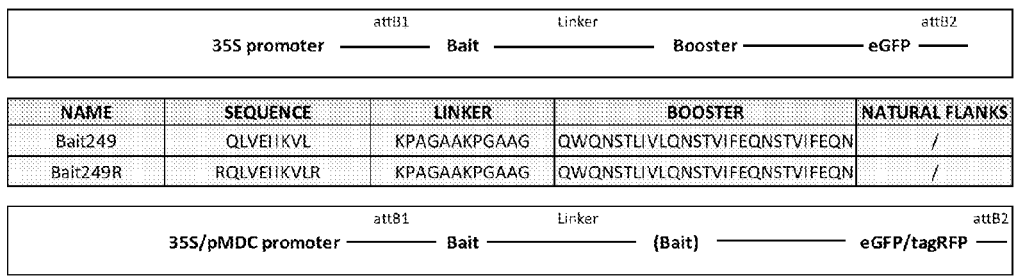
Figure 1C:
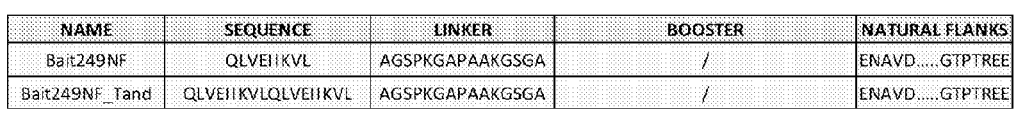

The GSK3-like kinase BIN2 was selected as a suitable plant target because of its cytosolic and nuclear localization that could permit a targeting by the expressed aggregating peptides (i.e. interferor peptides). We identified two short amino acidic stretches in the BIN2 primary amino acid sequence (see FIG. 1*a*) with the TANGO algorithm. These two beta-aggregation prone amino acid sequences were predicted to have a propensity to aggregate higher than 50%. These interferor peptides, also designated herein further as baits, cover the BIN2 regions from 44-55aa (bait44) and in the kinase domain from 249-257aa (bait249). For experimental reasons we decided to focus our study on bait249. To induce BIN2 aggregation, several constructs wherein bait249 was C-terminally fused to eGFP fluorescent protein were engineered in plant binary expression vectors. These bait249 expressing constructs have been engineered with and without positively charged amino acids (herein designated as gatekeepers); the construct comprising gatekeepers was designated as "bait249R" and the construct without these gatekeepers was designated as "bait249". The latter constructs were made to evaluate their role in enhancing the cytosolic localization of the expressed bait. In addition, a synthetic sequence know to boost the aggregation process (herein designated as booster) has been inserted between the bait and the eGFP through a linker sequence (the specific sequences are depicted in FIG. 1*b*).

To evaluate which biochemical features of the aggregating peptides were more optimal in achieving aggregates formation and specific targeting, different variants of the bait249 have also been further engineered. Two constructs expressing the bait249, flanked by 5-7aa naturally flanking the bait sequence in the BIN2 protein, inserted either in single copy (designated as bait249NF) or in tandem repeat (designated as bait249NF_Tand) have been generated. In this second set of vectors no booster of aggregation was inserted (see FIG. 1*c*).

2. Visualization of Bait249 Aggregation by Transient Expression in *N. benthamiana* Leaves The ability of the different baits to induce the formation of aggregates in plants has been initially checked with the Confocal Laser Scanning Microscope (CLSM) in a transient expression system by overexpressing the baits through *Agrobacterium tumefaciens*-mediated infiltration in *Nicotiana benthamiana* leaves. It was observed that the absence of gatekeepers in the bait249 vector strongly induced the formation of insoluble inclusion bodies rather than cytosolic expression (as witnessed in FIG. 2a). Conversely the bait249R induced a very strong cytosolic perinuclear aggregation as clearly shown by comparing the effect with the free GFP localization pattern (see FIG. 2b,e). The signal detected was more uniform than for bait249 and no inclusion bodies were identified. On the other hand the second set of constructs used in this study showed a clear presence of perinuclear aggregates in both versions, wherein the construct expressing the bait in tandem repeats (bait249NF_Tand) was the strongest aggregating construct as observed with the CLSM (see FIG. 2c,d). In these constructs it appears that the extra flanking amino acids, added to the bait sequences, play an important role in achieving cytosolic aggregation.

3. Bait259 Co-Localizes and Physically Interacts with the BIN2 Target Protein in *N. benthamiana* Cells A transient co-localization assay in *N. benthamiana* leaves of BIN2 and bait249 has been performed to have a fast indication of the bait targeting and co-aggregation tendency towards its target. Thereto, leaves were co-injected with *A. tumefaciens* strains expressing the bait249 strongest aggregating version as observed at the CLSM level, i.e. bait249NF_Tand fused to a RFP fluorescent protein and BIN2 protein fused to eGFP. The expression of the bait249NF_Tand was induced 24 hours before the subsequent fluorescence microscopy evaluation. CLSM analysis of leaves 4-5 days after injection showed a clear co-localization between the bait and the target evidenced both by overlapping expression patterns than by the calculated co-localization Mander's coefficients with values higher than 0.8. The formation of co-localizing cytosolic aggregates was also assessed in fluorescence microscopy (see FIG. 3). In a next step, after CLSM confirmation of co-localization and protein aggregation between the bait-GFP proteins and the BIN2 target, their stable physical interaction in a transient expression system was also assessed by co-immunoprecipitation (co-IP) experiments. To circumvent the lack of a specific BIN2 antibody the target protein was N-terminally fused to a haemaglutinin (HA) immunological tag. *N. benthamiana* leaves were then co-injected with *Agrobacterium* strains transformed with different bait249-GFP expressing vectors and the BIN2-HA was expressed under control of the 35S promoter. Both the bait249 with and without gatekeepers (and with booster of aggregation) and the bait249 in single and in tandem repeats (without booster) were tested. The co-IP experiment was performed by pull down of the GFP tagged baits by anti-GFP agarose coupled beads and subsequent Western blot detection was achieved with an anti-HA monoclonal antibody. Different negative controls were used: i) to test for unspecific binding of GFP to the beads a freeGFP encoding vector was co-injected with BIN2HA; ii) to test for unspecific binding of the synthetic booster to the beads a vector encoding only the booster and the linker sequence fused to GFP has been engineered and co-injected with BIN2-HA, iii) to test for unspecific binding either of the BIN2 protein or of the HA tag to the beads the BIN2-HA construct was injected alone; and iv) also a wild type plant extract has been used as additional negative control. The co-IP experiment indicated a positive interaction for any version of the bait249 tested with BIN2 thereby strongly demonstrating that the bait and the target can interact via the formation of a specific biochemical interaction, i.e. a cross-β-sheet-mediated aggregation (see FIG. 4). This result confirmed what was observed in the co-localization assays thereby generating proof of concept that a physical interaction between the two partners occurs in an in vivo system.

4. Assessing the Efficiency of Protein Aggregation in *Arabidopsis transgenic* Plants After transformation of the several GFP tagged bait249 expressing constructs the efficiency of aggregation was also monitored in transgenic *Arabidopsis* plants.

The evaluation of the induced aggregator complexes was assessed by imaging the GFP fluorescent protein at the CLSM microscope in each homozygous line.

It was observed that the 35S::bait249R-GFP and the 35S::bait249NF_Tand-GFP expressing lines showed the strongest subcellular GFP expression pattern with a clear perinuclear aggregation in different seedlings tissues (cotyledons, petioles, hypocotyls, and root) (see FIG. 5a-d, e-h).

In contrast, for the *Arabidopsis* plants comprising the 35S::bait249-GFP construct, the absence of gatekeepers impaired the expression of any cytosolically localized aggregates in *Arabidopsis* cells leading to a weaker expression of the reporter protein and the formation of round-shaped insoluble bodies in the cells, as was also observed in transiently transformed leaves of *Nicotiana*. The 35S::bait249NF-GFP expression pattern was weaker than for the bait in tandem (see FIG. 6a-h). For the abovementioned reasons the constructs 35S::bait249-GFP and 35S::bait249NF-GFP have not been considered for further functional analyses.

To investigate at the subcellular level the 35S::bait249R-GFP and 35S::bait249NF_Tand-GFP localization pattern in *Arabidopsis* cells, Transmission Electron Microscopy (TEM) was performed on seedlings 8 days after sowing (D.A.S.) stably expressing these constructs. The cytosolic bait-GFP localization pattern of the lines selected for further analyses have been confirmed by immunogold labeling experiments. In this approach labeling of hypocotyls and root cells in 35S::bait249R-GFP line with an anti-GFP antibody resulted in specific subcellular localization of the bait mainly in the cytosol of cells belonging to the root elongation area. The aggregating proteins appeared to be arranged both in fibrillar structures than in clustered agglomerations indicating that the aggregates can acquire different shapes in the cells (FIG. 7a-c). Golgi stacks were free from gold particles (see FIG. 7c) that instead appear to be more abundant in membrane-like structures (i.e. the ER) (FIG. 14b). The presence of free cytosolic bait249RGFP protein was also rarely found. For 35S::bait249NF_Tand-GFP a massive cytosolic and perinuclear localization was noticed in palisade cells in cotyledons and in root elongation area cells and no peculiar aggregator complexes shapes were detected (FIG. 7d-e).

Figure 8A:
Figure 8B:
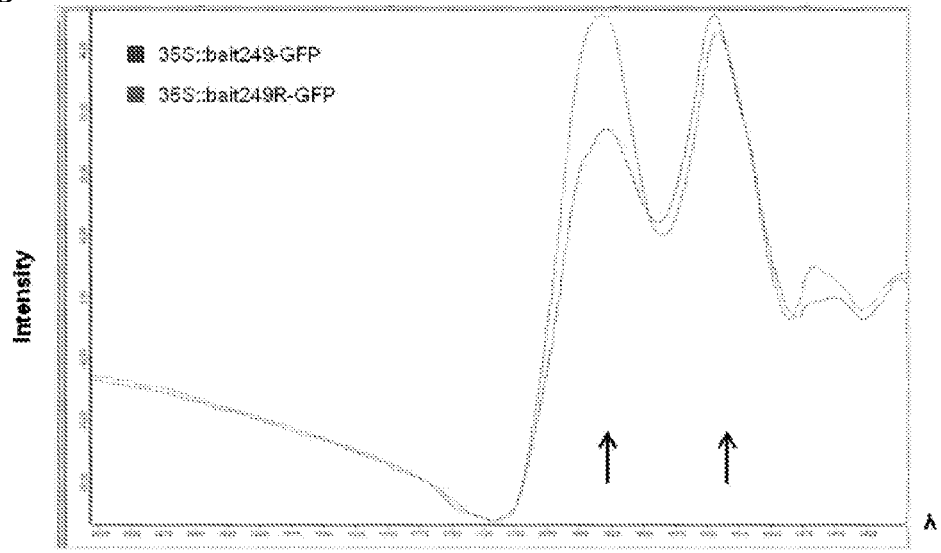

Biochemical confirmation of aggregator proteins levels has been assessed for each *Arabidopsis* transformed line by Native-PAGE electrophoresis and subsequent Western blot analysis with an anti-GFP monoclonal antibody (see FIG. 8a).

Figure 8C:
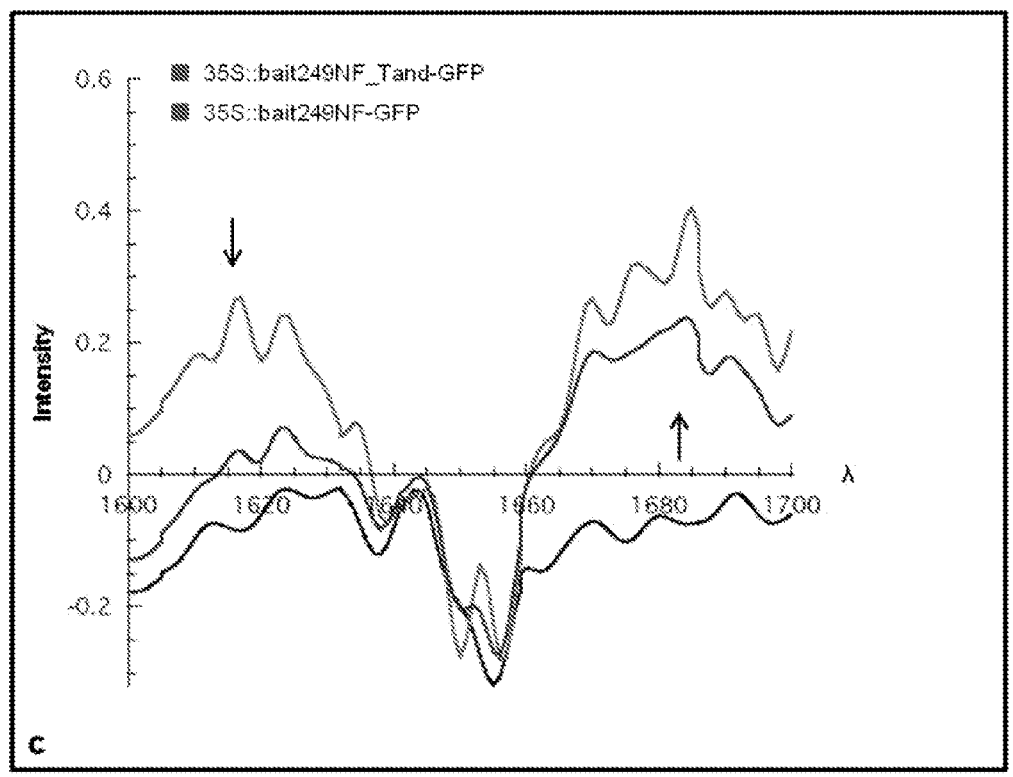

The biochemical nature of the aggregates has been then further analyzed by Fourier Transform-Infra Red (FT-IR) Spectroscopy after their immunoprecipitation (IP) with anti-GFP antibody. FT-IR spectra clearly showed two peaks in absorbance at 1616 and 1680λ values indicating a high content of β-sheets aggregates in 35S::bait249R-GFP and 35S::bait249-GFP lines, besides their different subcellular localization pattern (see FIG. 8b). For lines 35S::bait249NF-GFP and 35S::bait249NF_Tand-GFP a slighter increase in 1616 and 1680 absorption values was detected indicating a β-sheet content in the immunoprecipitated material, although at a lesser extent than for the previously analyzed lines (FIG. 8c).

4.1 Phenotype of Transgenic *Arabidopsis* Plants

Figure 9A:
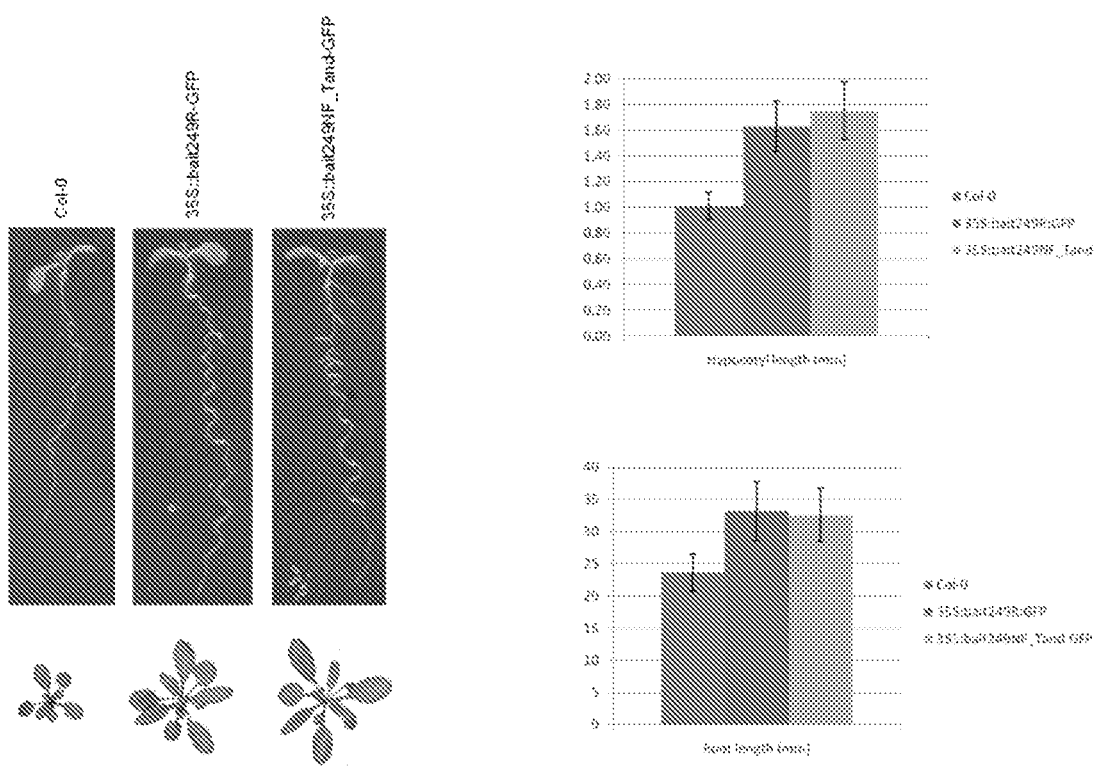
Figure 9B:
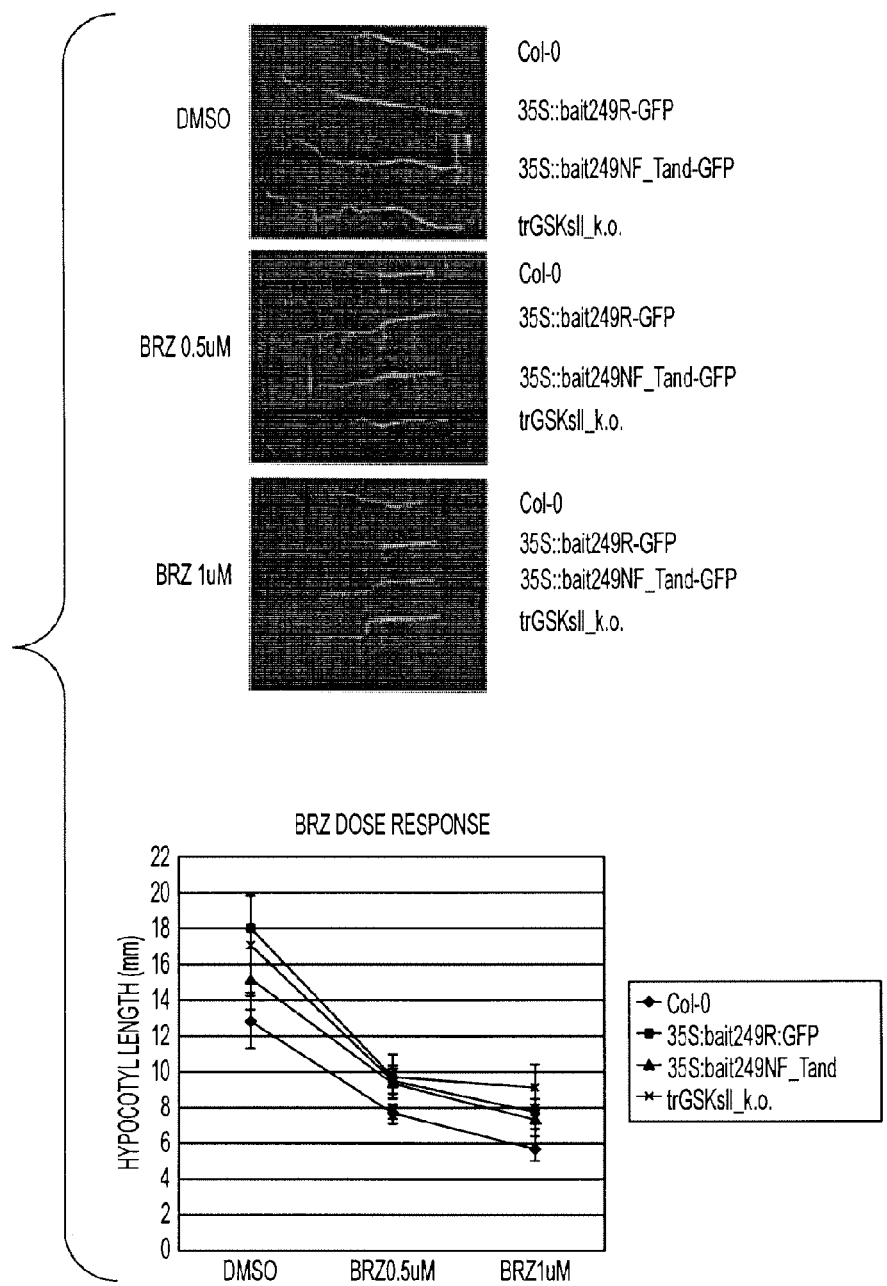

The homozygotic bait249 expressing lines were then further analyzed both in vitro and in soil for the appearance of phenotypes showing that a knock-down in BIN2 was occurring. The 35S::bait249R-GFP and 35S::bait249NF_Tand-GFP transgenic seedlings, vertically grown for 8 days in vitro, had longer roots and hypocotyls than the untransformed line Col-0; this observation was also confirmed by quantification with the ImageJ software (FIG. 9a). The statistical evaluation performed indicated a statistical significance between Col-0 and transgenic lines. One month old transgenic plants grown in soil also resulted in bigger individuals with respect to Col-0 (FIG. 9a). The 35S::bait249-GFP and 35S::bait249NF-GFP transgenic seedlings did not show any phenotypical difference with Col-0 neither in vitro nor in soil conditions and were not included in the further analysis.

In a next step, to provide further evidence that the BIN2 function is affected by its specific aggregation, 35S::bait249R-GFP and 35S::bait249NF-GFP lines were examined for resistance to the brassinosteroid biosynthesis inhibitor, brassinazole (BRZ). As a positive control the triple mutant knock-out in BIN2 and its two close homologues (atsk22 and atsk23) was used (Vert G and Chory J (2006) *Nature* 441 (7089): 96-100). We expected that if the function of BIN2 was affected it would result in plants being at least partially resistant to brassinazole (please note that the triple mutant (Vert G and Chory J (2006) *Nature* 441 (7089): 96-100) is resistant to brassinazole. We could indeed show that the transgenic lines showed a partial resistance to the inhibitor brassinazole, as quantified in terms of hypocotyl length (see FIG. 9b).

4.2 Gene Expression Changes in Transgenic *Arabidopsis* Plants

In a quantitative real-time PCR (qRT-PCR) analysis on BRs-related DWF4 and CPD gene expression we demonstrated a decreased expression level of DWF4 in the two aggregator lines. In the case of the CPD gene expression, an effect was only observed for 35S:bait249NF_Tand:GFP, indicating a feedback inhibition, and thus an activated BRs signaling (see FIG. 10a). Accordingly, the analysis of the relative expression levels of a BR-responsive transcription factor from the NAC family showed a slightly increased expression for the 35S:bait249NF_Tand:GFP construct (see FIG. 10a).

Figure 10B:
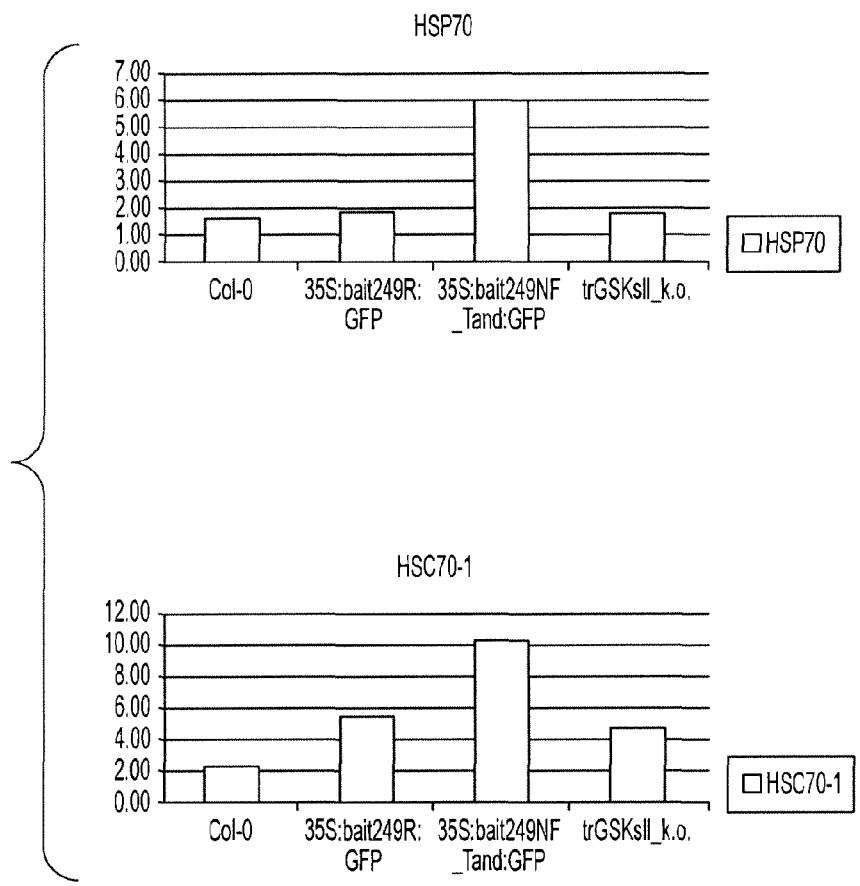
Figure 10B:
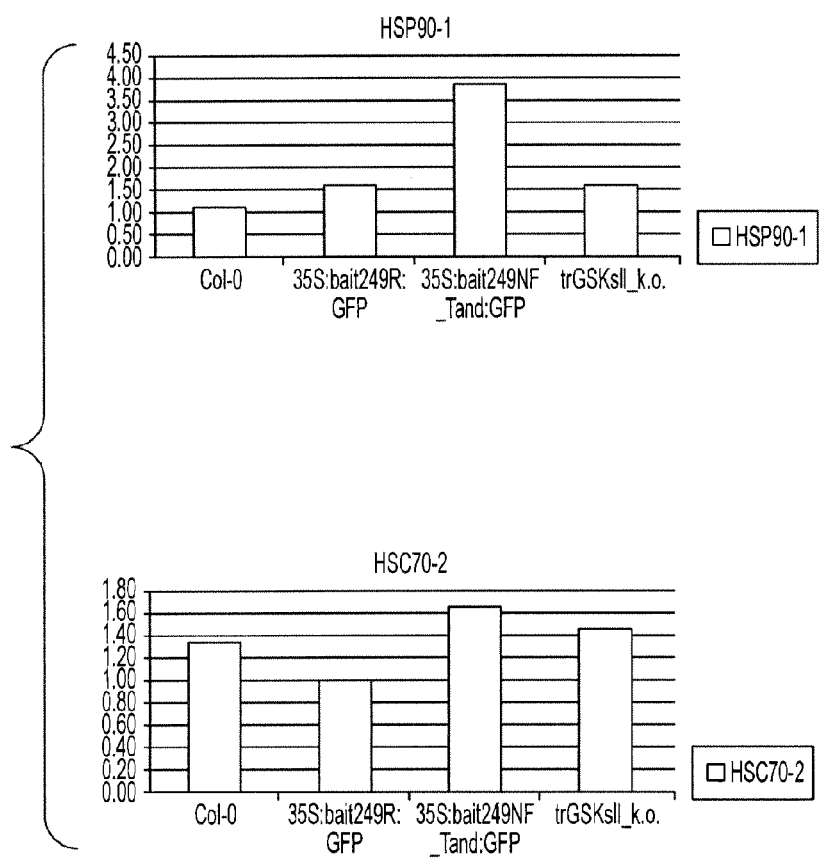
Figure 10B:
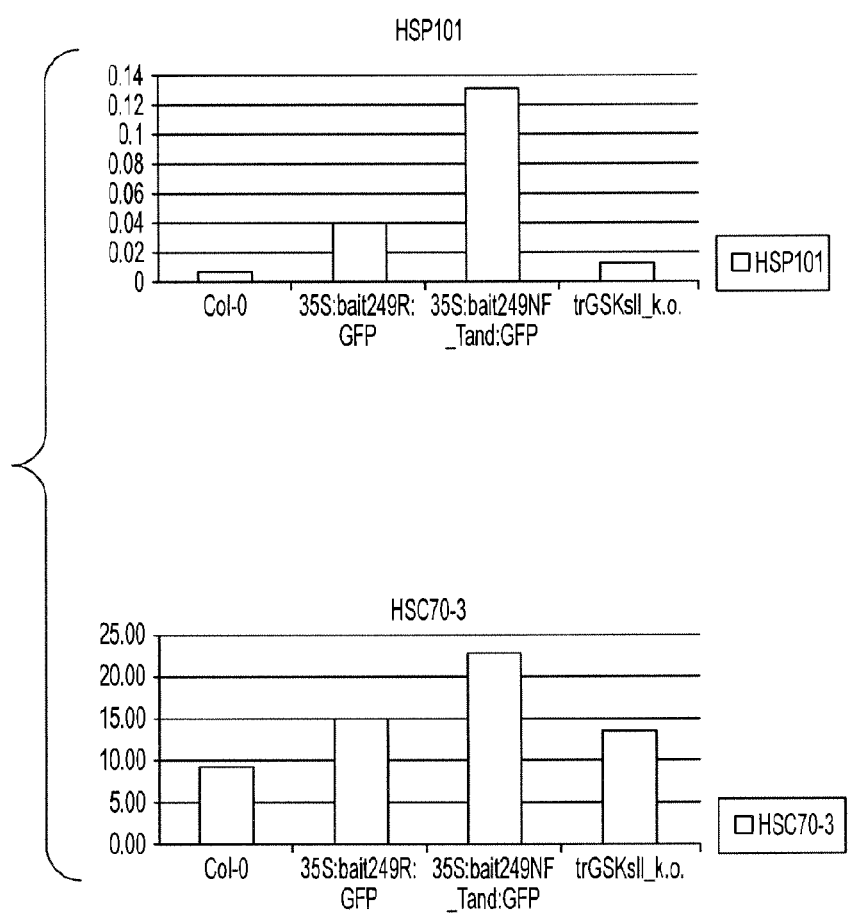

Besides BR-related genes, the effect of 35S::bait249R-GFP and 35S::bait249NF_Tand-GFP expression in transgenic *Arabidopsis* lines in the induction of the expression of chaperone proteins was also monitored. Interestingly, the two aggregator lines, but in particular the transgenic plant expressing the bait249 in tandem repeats (35S::bait249NF_Tand-GFP) showed higher (induced) expression levels of HSP70, HSP90-1, HSP101, HSC70-1, HSC70-2 and HSC70-3 genes (see FIG. 10b).

4.3 Morphological Evaluation of Transgenic *Arabidopsis* Plants

In addition a morphological evaluation at the transmission electron microscopy (TEM) level of the transgenic lines was performed to monitor a possible cytotoxic effect of the aggregator constructs at the subcellular level. With this approach no peculiar alteration in size and shapes of cells and subcellular organelles could be observed in different tissues of the 35S::bait249R-GFP line (see FIG. 11). Occasionally a larger amount of plastoglobuli was found in chloroplasts of the transgenic line. The latter phenomenon is usually an indication of stress which in the present case could also be caused by the in vitro growth conditions on nylon meshes. TEM evaluation is also performed on the homozygotic line expressing the bait249 in tandem repeats without booster of aggregation.

To assess the co-localization of the target protein and the bait in stably transformed *Arabidopsis* lines, we aimed to visualize the co-localization between 35S::BIN2-GFP with the strongly expressed aggregator variant bait249NF_Tand fused to tagRFP fluorescent protein expressed under an inducible promoter (pMDC::bait249NF_Tand-RFP). To this end the best 35S::BIN2-GFP expressing line was super-transformed with the estradiol inducible pMDC::bait249NF_Tand-RFP construct. The co-localization assays were performed on the primary transformants after 24 hours of bait249NF_Tand induction and then analyzed at the CLSM. The confocal analysis of 8 D.A.S. transformed seedlings showed a clear overlapping localization pattern of the bait and the target (see FIG. 12). The intensity of the co-localization observed was also quantified with an ad hoc software (ImageJ MBF) which released Mander's coefficients close to 1 for all the pictures processed, meaning that a high co-localization between the bait and the target protein occurred.

Materials and Methods for the Examples Section

1. Cloning of Bait259 Aggregator in Plant Compatible Gateway Vectors

By using the TANGO prediction tool (http://tango.switchlab.org/), two aggregator peptides that target two different bait regions (44-55aa: RVVGTGSFGIVFK (SEQ ID NO:1); 249-257aa: QLVEIIKVL (SEQ ID NO:2)) in the BIN2 protein were initially selected. For BIN2 region 249-257aa, the aggregator constructs were designed both with (bait249R: RQLVEIIKVLR (SEQ ID NO:3)) and without (bait249: QLVEIIKVL) flanking gatekeepers, represented by positively charged arginine residues.

The respective bait sequences were C-terminally fused to a synthetic sequence booster of aggregation (QWQNSTLIVLQNSTVIFEQNSTVIFEQN (SEQ ID NO:4)) by PCR analysis, introducing a flexible linker sequence KPAGAAKPGAAG (SEQ ID NO:5).

By using the rationale of checking which bait amino-acidic modifications could lead to better targeting of the BIN2 protein, two other vectors expressing the bait249 were then generated. The bait249 was modified by adding 5-7aa naturally flanking the 249-257aa region in BIN2 (bait249NF: ENAVDQLVEIIKVL GTPTREE (SEQ ID NO:6)), as well as 6 amino acids (MADDKE (SEQ ID NO:7)) corresponding to the beginning of the BIN2 protein sequence. The flexible linker sequence has been changed to AGSPKGA-PAAKGSGA (SEQ ID NO:8) and the booster sequence removed. In one construct the bait has been inserted in tandem repeat (bait249NF_Tand: ENAVDQLVEIIKVL GTPTREEENAVDQLVEIIKVLGTPTREE (SEQ ID NO:9)). The resulting DNA sequences were Gateway cloned in pDONR221 entry vectors. After sequence confirmation, the inserts were transferred to the pK7WG2,0 (Karimi et al. 2007) destination vector to generate plant binary vectors containing the 35S promoter and the heterologous sequence C-terminally fused to eGFP fluorescent tag. The bait249NF_Tand was also cloned in a Gateway pMDC-m13GW vector containing an estradiol inducible promoter (Curtis and Grossniklaus 2003) and the heterologous sequence has been inserted C-terminally fused to tagRFP fluorescent protein (pMDC::bait249NF_Tand-tagRFP). The 35S::BIN2-HA vector has been engineered by using pKWG2,0 destination vector to generate plant binary vectors containing the 35S promoter and the heterologous sequence that was C-terminally fused by homologous recombination to an HA fluorescent tag.

2. Plant Materials and Growth Conditions

*N. benthamiana* plants were grown directly in soil under a 16L/8D photoperiod at 21° C. for 45 days and infiltrated before flowering.

*Arabidopsis thaliana* L. (Heyhn.) (Columbia ecotype, Col-0) seedlings were stratified for 2 days at 4° C. and germinated in square plates on vertical half-strength Murashige & Skoog (MS) medium (Duchefa) containing 1% sucrose and 0.8% agar, pH 5.9, at 22° C. in a 16-h/8-h light-dark cycle with a light intensity of 80 to 100 mE m$^{-2}$ s$^{-1}$ supplied by cool-white fluorescent tubes (Spectralux Plus 36W/840; Radium) except when indicated. Seedlings grown in vitro for 21 days were transferred to soil in growth room with similar light and temperature conditions. The following mutant line was used in this study: bin2-3/atsk22/atsk23 triple mutant (Vert and Chory 2006). Previously described transgenic lines used in the study are: pBIN2::BIN2-GFP and 35S::B/N2-GFP (Vert and Chory, 2006). Brassinazole (BRZ) was purchased from TCI EUROPE N.V. (Belgium), 24-Epibrassinolide (BL) from Fuji Chemical Industries (Japan). The expression of pMDC::bait249NF_Tand-RFP was induced by adding or infiltrating 20 µM Estradiol (Sigma) for 24 h.

3. Plants Transformation

To generate stable *A. thaliana* transgenic plants, the engineered constructs were transformed in *A. tumefaciens* C58C1 strain. Suspensions of the transformed bacterial strains were then used to dip *A. thaliana* Col-0 wild-type floral buds. Primary transformants were selected by germinating the seeds of the transformed flowers on antibiotic-selective medium. Trough 3:1 segregation analysis of the next generation homozygotic transgenic lines were further isolated. For agroinfiltrations *N. benthamiana* leaves were injected with *A. tumefaciens* strains C58C1(pCH32) transformed with vectors 35S::bait249R-GFP, 35S::bait249-GFP, 35S::bait249NF-GFP, 35S::bait249NF_Tand-GFP, pMDC:bait249NF_Tand-RFP together with 35S::P19, encoding the silencing inhibitor protein p19 derived from the *Tomato Bushy Stunt Virus* (Voinnet et al. 2003).

The strains were used to co-infiltrate, with a syringe without needle, the abaxial side of *N. benthamiana* leaves following a previously published protocol with minor modifications (English et al. 1996). Briefly, bacteria were grown overnight at 28° C. in YEB medium containing 10 mM 2-(N-morpholino)ethanesulfonic acid pH 5.5 and 20 µM acetosyringone. At the optical density (O.D.) of 0.8 bacteria were pelletted, resuspended in 10 mM MES, 10 mM MgCl$_2$, 100 µM acetosyringone and kept at room temperature for 3 hours before infiltration.

4. Imaging and Image Analysis

Seedlings were imaged on a laser scanning confocal microscope (Olympus FluoView 1000) with a 20× or a 60× water immersion lens, NA1.2. Image analysis was done with Olympus FluoView FV10-ASW software. For co-localization experiments, Mander's overlap coefficient calculations were done with ImageJ MBF software.

5. Tissue Fixation and Immunological Labeling for Electron Microscopy

For morphological studies, fragments (1-2 mm$^2$) of cotyledons, hypocotyls and roots of 35S::bait249R-GFP and 35S::bait249NF_Tand-GFP 8 days after sowing (D.A.S.) seedlings were immersed in a fixative solution of 4% paraformaldehyde and 2.5% glutaraldehyde and postfixed in 1% OsO$_4$ with 1.5% K$_3$Fe(CN)$_6$ in 0.1 M NaCacodylate buffer, pH 7.2. Samples were dehydrated through a graded ethanol series, including a bulk staining with 2% uranyl acetate at the 50% ethanol step followed by embedding in Spurr's resin. Ultrathin sections were made using an ultramicrotome (Leica EM UC6) and post-stained in a Leica EM AC20 for 40 min in uranyl acetate at 20° C. and for 10 min in lead stain at 20° C. Grids were viewed with a JEM 1010 transmission electron microscope (JEOL, Tokyo, Japan) operating at 80 kV.

For immunocytochemical detection, fragments (1-2 mm$^2$) of cotyledons, hypocotyls and roots of 35S::bait249R-GFP and 35S::bait249NF_Tand-GFP 8 D.A.S. seedlings were immersed in a fixative solution of 2.5% paraformaldehyde and 0.3% glutaraldehyde in 0.1 M NaCacodylate buffer, pH 7.2. Samples were dehydrated through a graded ethanol series and infiltrated stepwise over 3 d at 4° C. in LR-White, hard grade (London Resin), followed by embedding in capsules. Polymerization was done by UV illumination for 24 h at 4° C. followed by 16 h at 60° C. Ultrathin sections of gold interference colour were cut with an ultramicrotome (Leica EM UC6) and collected on formvar-coated copper slot grids. All steps of immunolabeling were performed in a humid chamber at room temperature. Grids were floated upside down on 25 µl of blocking solution (5% (w/v) bovine serum albumin (BSA), for 30 min followed by washing five times for 5 min each times with 1% BSA in PBS. Incubation in a 1:50 dilution (1% BSA in PBS) of primary antibodies anti-GFP rabbit (AbCam) for 60 min was followed by washing five times for 5 min each time with 0.1% BSA in PBS. The grids were incubated with PAG 10 nm 1:60 dilution (1% BSA in PBS) (Cell Biology, Utrecht University, The Netherlands) and washed twice for 5 min each time with 0.1% BSA in PBS, PBS, and double-distilled water. Sections were post-stained in a Leica EM AC20 for 40 min in uranyl acetate at 20° C. and for 10 min in lead citrate at 20° C. Grids were viewed with a JEM 1010 transmission electron microscope (Jeol Ltd., Tokyo, Japan) operating at 80 kV.

6. Electrophoresis and Western Blot

Total soluble proteins (TSP) were extracted from *Arabidopsis* 8 D.A.S. seedlings or fragments of *N. benthamiana* agroinfiltrated leaves were grinded in a mortar and rinsed with ice-cold 0.01 M phosphate buffered saline (PBS; 10 mM Na$_2$HPO$_4$, 10 mM NaH$_2$PO$_4$, 150 mM NaCl, pH 7.2), added of proteases inhibitors (Complete® EDTA free, Roche, Germany). The homogenates were then centrifuged at 20,000×g for 20' at 4° C. Supernatants were quantified for protein content with the Bradford assay (Micro Assay kit, Bio-Rad Laboratories Inc., Hercules, Calif., U.S.A.).

The co-immunoprecipitation experiment has been carried out by using agarose-coupled anti-GFP beads (Chromotek) according to the manufacturer instructions.

Whole protein extracts or IP products were fractionated either by SDS-PAGE (Biorad) or BN-PAGE (NativePAGE system, Invitrogen) following the product manuals. For SDS-PAGE, approximately 60 µg of TSP were denatured at 95° C. for 10 min in the presence of 1% SDS and 0.1M DTT and then fractionated by 10%, 12% or 15% (w/v) SDS-PAGE gels in TGS running buffer (25 mM Tris, 192 mM glycine and 0.1% SDS). Membranes were blocked overnight with 5% (w/v) nonfat milk in PBS at 4° C. before immunoblotting.

For BN-PAGE, protein extract was added with 20% glycerol and 5 mM Coomassie G-250 before loading onto 3-12% Novex Bis-Tris gradient gels. The electrophoresis was performed in a running buffer containing 50 mM BisTris and 50 mM Tricine (plus 0.004% Coomassie G-250 in cathode buffer) under fixed voltage (100 V) at 21° C. for 120 min. Proteins were transferred onto polyvinylidene fluoride membranes and stained with Coomassie G-250 to show molecular-weight markers (NativeMark, Invitrogen). After fixation with 8% acetic acid for 20 min, the polyvinylidene fluoride membranes were air dried and destained with 100% methanol. Membranes were blocked overnight with 4% BSA in TBS at 4° C. before immunoblotting. To detected HA tagged BIN2 or GFP tagged bait249, bait249R, bait249NF, bait249NF_T and on the membrane, the primary antibodies (rat anti-HA, Roche; mouse anti-GFP, Living Colors) have been diluted to 1:1,000 or 1:5,000 respectively in PBS containing 0.1% Tween-20 (PBS-T) and 3% (w/v) nonfat milk and incubated for 1 h at RT. After four rinses with PBS-T, the membrane was stained with horseradish peroxidase (HRP)-conjugated goat anti-rat IgG (GE-Healthcare) or sheep anti-mouse IgG (GE-Healthcare) or and visualized with electrochemical luminescence system.

7. qRT-PCR

RNA was extracted from whole 8 D.A.S. seedlings treated as indicated in 0.5 MS medium and RNA was extracted using the RNeasy kit (Qiagen) according to the supplier's instructions and quantified on a NanoDrop® ND-100 Spectrophotometer. Poly(dT) cDNA was prepared from 1 μg of total RNA with iScript reverse transcriptase (Biorad). PCR was performed on 384-well reaction plates, which were heated for 10 min to 95° C., followed by 45 cycles of denaturation for 10 s at 95° C. and annealing and extension for 15 s at 60° C. and 72° C., respectively. Target quantifications were performed with specific primer pairs listed in Table 1. All PCRs were done in three technical repeats, and at least two biological repeats were used for each sample. For chaperones expressions analysis Taqman primer triplets were purchased from Integrated DNA Technologies (IDT). qRT-PCR was performed using the Applied Biosystems Fast Realtime PCR mixture in a Biorad iQ5 machine with detection of the Fam fluorophore. Relative expression levels were normalized to CDKA and EF expression levels.

TABLE 1

Primers used for qRT-PCR analysis

| Primer | SEQ ID NO | Sequence |
|---|---|---|
| DWF4FOR | 10 | GTGATCTCAGCCGTACATTTGGA |
| DWF4REV | 11 | CACGTCGAAAAACTACCACTTCCT |
| CPDFOR | 12 | GAATGGAGTGATTACAAGTC |

TABLE 1-continued

Primers used for qRT-PCR analysis

| Primer | SEQ ID NO | Sequence |
|---|---|---|
| CPDREV | 13 | GTGAACACATTAGAAGGGCCTG |
| NACFOR | 14 | CTCATTTGCCAATCCTGTATC |
| NACREV | 15 | GCACTGAGATGCGACATCTTG |
| HSP70FOR | 16 | TGACTCTTATCCGCTTGAACAG |
| HSP70REV | 17 | TCCTACGTTGCTTTCACTGAC |
| HSP90-1FOR | 18 | GTGGTTCCTTCACTGTCACTAG |
| HSP90-1REV | 19 | TTCACCAAGTCTTTGAGTCTCC |
| HSP101FOR | 20 | TGAAAGGAAGAGGATGCAGC |
| HSP101REV | 21 | TGTATTTCATCGTGAGAGGCTG |
| HSC70-1FOR | 22 | GCTATTCTCAGCGGTGAAGG |
| HSC70-1REV | 23 | TTCTCGTCTTGGATGGTGTTC |
| HSC70-2FOR | 24 | GAAACAGAACCACTCCCTCG |
| HSC70-2REV | 25 | CCAATCAACCTCTTTGCATCG |
| HSC70-3FOR | 26 | AACAGAACCACACCGTCTTAC |
| HSC70-3REV | 27 | ACCAATCAACCTCTTCGCATC |
| CDKAFOR | 28 | ATTGCGTATTGCCACTCTCATAGG |
| CDKAREV | 29 | TCCTGACAGGGATACCGAATGC |
| EFFOR | 30 | CTGGAGGTTTTGAGGCTGGTAT |
| EFREV | 31 | CCAAGGCTGAAAGCAAGAAGA |

8. FT-IR Spectroscopy

Fourier Transform Infrared Spectroscopy has been performed on a Tensor 37 FT-IR spectrometer equipped with a BioATR II cell (Bruker) as previously reported (Xu et al.). Briefly, the detector was cooled with liquid nitrogen, and the Bio-ATR II cell was purged by a continuous flow of dried air to minimize water vapour that may interfere with the results. Before and after each measurement, the crystal of the ATR cell was washed with ethanol and water. Samples were measured against background composed of buffer-covered crystal.

The invention claimed is:

1. A method for down-regulating the biological function of a protein in a host, the method comprising:
   i) acquiring the amino acid sequence of a target protein of interest;
   ii) utilizing a mathematical algorithm to determine an aggregation propensity score and to identify a β-aggregation region within the amino acid sequence of the target protein;
   iii) isolating the β-aggregation region from the amino acid encoding sequence of the target protein;
   iv) producing a non-naturally occurring molecule comprising the isolated β-aggregation region;
   v) contacting, within a host, the target protein with the non-naturally occurring molecule comprising the isolated β-aggregation region;
   vi) assaying or monitoring for cross β-aggregation between the non-naturally occurring molecule comprising the isolated β-aggregation region and the target protein of interest; and
   vii) selecting for a host having reduced activity of the target protein relative to a corresponding wild-type-host that does not comprise the non-naturally occurring molecule comprising the isolated β-aggregation region.

2. The method according to claim 1, wherein said β-aggregation region consists of at least 3 contiguous amino acids.

3. The method according to claim 1, wherein said non-naturally occurring molecule is a polypeptide encoded by a nucleic acid present in a recombinant vector and which, upon introduction into a plant cell, plant seed or plant, produces said polypeptide in said plant cell, plant seed or plant.

4. The method according to claim 1, wherein said β-aggregation region in said non-naturally occurring molecule is fused to a moiety that prevents self-aggregation of said β-aggregation region.

5. The method according to claim 4, wherein said moiety is a peptide or a protein domain.

6. The method according to claim 4, wherein a polypeptide linker is present between said β-aggregation region and said moiety.

7. The method of claim 1, wherein said protein is down-regulated in a plant, plant cell, or plant seed.

8. A method for producing a plant, plant cell or plant seed in which the biological function of a protein is down-regulated, said method comprising:
   i) acquiring the amino acid sequence of a target protein of interest;
   ii) utilizing a mathematical algorithm to determine an aggregation propensity score and to identify a β-aggregation region within the amino acid sequence of the target protein;
   iii) isolating the β-aggregation region from the amino acid sequence of the target protein;
   iv) producing a non-naturally occurring molecule comprising the isolated β-aggregation region;
   v) contacting, within a plant, plant cell, or plant seed, the target protein with the non-naturally occurring molecule comprising the isolated β-aggregation region;
   vi) assaying or monitoring for cross β-aggregation between the non-naturally occurring molecule comprising the isolated β-aggregation region and the target protein of interest; and
   vii) selecting for a plant, plant cell, or plant seed having reduced activity of the target protein relative to a corresponding wild-type plant, plant cell or plant seed that does not comprise the non-naturally occurring molecule comprising the isolated β-aggregation region.

9. The method according to claim 8, wherein said non-naturally occurring molecule is a polypeptide encoded by a nucleic acid present in a recombinant vector and which, upon introduction into a plant cell, plant seed or plant, produces said polypeptide in said plant cell, plant seed or plant.

* * * * *